(12) United States Patent
Kumada et al.

(10) Patent No.: US 8,883,985 B2
(45) Date of Patent: Nov. 11, 2014

(54) ANTIBODY-IMMOBILIZED CARRIER, METHOD OF PRODUCING ANTIBODY-IMMOBILIZED CARRIER, AND USE OF SAID ANTIBODY-IMMOBILIZED CARRIER

(75) Inventors: Yoichi Kumada, Kyoto (JP); Michimasa Kishimoto, Kyoto (JP); Kyoko Hamasaki, Kyoto (JP); Aya Nakagawa, Kyoto (JP)

(73) Assignees: National University Corporation Kyoto Institute of Technology, Kyoto-Shi (JP); Denka Seiken Co., Ltd., Tokyo (JP)

( * ) Notice: Subject to any disclaimer, the term of this patent is extended or adjusted under 35 U.S.C. 154(b) by 0 days.

(21) Appl. No.: 13/578,974

(22) PCT Filed: Feb. 15, 2011

(86) PCT No.: PCT/JP2011/053157
§ 371 (c)(1),
(2), (4) Date: Aug. 14, 2012

(87) PCT Pub. No.: WO2011/102342
PCT Pub. Date: Aug. 25, 2011

(65) Prior Publication Data
US 2012/0309943 A1    Dec. 6, 2012

(30) Foreign Application Priority Data
Feb. 16, 2010   (JP) ................. 2010-031684

(51) Int. Cl.
| | | |
|---|---|---|
| C07K 17/02 | (2006.01) | |
| C07K 7/06 | (2006.01) | |
| C07K 7/08 | (2006.01) | |
| C12N 11/06 | (2006.01) | |
| C12N 11/08 | (2006.01) | |
| G01N 33/68 | (2006.01) | |
| C07K 16/00 | (2006.01) | |
| C07K 16/40 | (2006.01) | |
| C07K 16/28 | (2006.01) | |
| C07K 16/18 | (2006.01) | |
| C07K 16/30 | (2006.01) | |
| C07K 16/24 | (2006.01) | |

(52) U.S. Cl.
CPC ............. *C07K 16/00* (2013.01); *C07K 2317/21* (2013.01); *C07K 16/40* (2013.01); *C07K 16/2887* (2013.01); *C07K 16/18* (2013.01); *C07K 2317/515* (2013.01); *C07K 2317/55* (2013.01); *C07K 16/303* (2013.01); *C07K 2317/51* (2013.01); *C07K 16/249* (2013.01); *C07K 2317/24* (2013.01)
USPC ............. 530/389.1; 530/391.1; 530/370; 530/412; 530/300; 436/501; 436/532

(58) Field of Classification Search
None
See application file for complete search history.

(56) References Cited

U.S. PATENT DOCUMENTS

| | | | |
|---|---|---|---|
| 2002/0004587 A1* | 1/2002 | Miller et al. ............... | 530/388.8 |
| 2006/0252028 A1* | 11/2006 | Ueda et al. ..................... | 435/5 |
| 2010/0168393 A1 | 7/2010 | Clube et al. | |
| 2011/0045538 A1 | 2/2011 | Kumada et al. | |

FOREIGN PATENT DOCUMENTS

| | | |
|---|---|---|
| JP | 2009-511892 | 3/2009 |
| WO | 2009/101807 | 8/2009 |

OTHER PUBLICATIONS

Kumada et al., J Biotechnology 127: 288-299, 2007.*
Stryer et al., in Biochemistry, Third edition, W H Freeman Company, New York, pp. 31-33, 1998.*
Colman et al., in Research in Immunology (145(1):33-35, 1994.*
Kumada, Yoichi, et al., "Development of fast protein immunoassay using peptide with high affinity to polystyrene . . . ," Bioscience & Industry, Sep. 1, 2007, vol. 65, No. 9, pp. 460-462.
Sasaki, E., et al., "Development of antibody library by in vitro domain shuffling . . . ," Abstracts of 42nd Autumn Meeting of the Society of Chemical Engineers, Japan, Aug. 6, 2010, vol. 42, p. 109, LIP41.

* cited by examiner

*Primary Examiner* — Phuong Huynh
(74) *Attorney, Agent, or Firm* — Casimir Jones, S.C.

(57) ABSTRACT

The present invention provides an antibody-immobilized carrier that can be used in antibody screening, a method of producing the antibody-immobilized carrier, and use of the antibody-immobilized carrier. Efficient antibody screening can be carried out particularly by an antibody-immobilized carrier including two or more antibody immobilized regions onto each of which a heavy-chain low-molecular-weight antibody and a light-chain low-molecular-weight antibody are separately immobilized, the two or more antibody immobilized regions each being included in an independent manner, the heavy-chain low-molecular-weight antibody including a heavy-chain variable region, the light-chain low-molecular-weight antibody including a light-chain variable region, the heavy-chain low-molecular-weight antibody and the light-chain low-molecular-weight antibody each being derived from an antibody recognizing a different antigen.

15 Claims, 19 Drawing Sheets

(a)

(b)

SEQUENCE LISTING

```
<160> NUMBER OF SEQ ID NOS: 19

<210> SEQ ID NO 1
<211> LENGTH: 230
<212> TYPE: PRT
<213> ORGANISM: Mus musculus

<400> SEQUENCE: 1

Met Asp Val Gln Leu Gln Glu Ser Gly Pro Gly Leu Val Lys Pro Ser
1               5                   10                  15

Gln Ser Leu Ser Leu Thr Cys Thr Val Thr Gly Tyr Ser Ile Thr Ser
            20                  25                  30

Asp Tyr Ala Trp Asn Trp Ile Arg Gln Phe Pro Gly Asn Lys Leu Glu
        35                  40                  45

Trp Met Gly Tyr Ile Ser His Ser Gly Ser Thr Gly Tyr Asn Pro Ser
    50                  55                  60

Leu Lys Ser Arg Ile Ser Ile Thr Arg Asp Thr Ser Lys Asn Gln Phe
65                  70                  75                  80

Phe Leu Gln Leu Asn Ser Val Thr Glu Asp Thr Ala Thr Tyr Tyr
                85                  90                  95

Cys Ala Arg Gly Gly Lys Asn Trp Asp Ala Tyr Trp Gly Gln Gly Thr
                100                 105                 110

Leu Val Thr Val Ser Ser Lys Thr Thr Pro Pro Ser Val Tyr Pro Leu
            115                 120                 125
```

```
Ala Pro Gly Ser Ala Ala Gln Thr Asn Ser Met Val Thr Leu Gly Cys
    130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Glu Ser
                165                 170                 175

Asp Leu Tyr Thr Leu Ser Ser Val Thr Val Pro Ser Ser Pro Arg
            180                 185                 190

Pro Ser Glu Thr Val Thr Cys Asn Val Ala His Pro Ala Ser Ser Thr
            195                 200                 205

Lys Val Asp Lys Lys Ile Pro Arg Asp Cys Gly Ala Ala Ala Leu Glu
    210                 215                 220

His His His His His His
225                 230

<210> SEQ ID NO 2
<211> LENGTH: 239
<212> TYPE: PRT
<213> ORGANISM: Mus musculus

<400> SEQUENCE: 2

Met Asp Val Gln Leu Gln Glu Ser Gly Pro Gly Leu Val Lys Pro Ser
1               5                   10                  15

Gln Ser Leu Ser Leu Thr Cys Thr Val Thr Gly Tyr Ser Ile Thr Ser
            20                  25                  30

Asp Tyr Ala Trp Asn Trp Ile Arg Gln Phe Pro Gly Asn Lys Leu Glu
        35                  40                  45

Trp Met Gly Tyr Ile Ser His Ser Gly Ser Thr Gly Tyr Asn Pro Ser
    50                  55                  60

Leu Lys Ser Arg Ile Ser Ile Thr Arg Asp Thr Ser Lys Asn Gln Phe
65                  70                  75                  80

Phe Leu Gln Leu Asn Ser Val Thr Thr Glu Asp Thr Ala Thr Tyr Tyr
                85                  90                  95

Cys Ala Arg Gly Gly Lys Asn Trp Asp Ala Tyr Trp Gly Gln Gly Thr
            100                 105                 110

Leu Val Thr Val Ser Ser Lys Thr Thr Pro Pro Ser Val Tyr Pro Leu
        115                 120                 125

Ala Pro Gly Ser Ala Ala Gln Thr Asn Ser Met Val Thr Leu Gly Cys
    130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Glu Ser
                165                 170                 175

Asp Leu Tyr Thr Leu Ser Ser Val Thr Val Pro Ser Ser Pro Arg
            180                 185                 190

Pro Ser Glu Thr Val Thr Cys Asn Val Ala His Pro Ala Ser Ser Thr
            195                 200                 205

Lys Val Asp Lys Lys Ile Pro Arg Asp Cys Gly Ala Ala Ala Arg Ile
    210                 215                 220

Ile Ile Arg Arg Ile Arg Arg Ile Glu His His His His His His
225                 230                 235

<210> SEQ ID NO 3
<211> LENGTH: 226
<212> TYPE: PRT
<213> ORGANISM: Mus musculus
```

```
<400> SEQUENCE: 3

Met Asp Ile Lys Met Thr Gln Ser Pro Ser Ser Met Tyr Ala Phe Leu
1               5                   10                  15

Gly Glu Arg Val Thr Ile Thr Cys Lys Ala Ser Gln Asp Ile Asn Ser
                20                  25                  30

Tyr Leu Ser Trp Phe Gln Gln Lys Pro Gly Lys Ser Pro Lys Thr Leu
            35                  40                  45

Ile Tyr Arg Ala Asn Arg Leu Val Asp Gly Val Pro Ser Arg Phe Ser
50                  55                  60

Gly Ser Gly Ser Gly Gln Asp Tyr Ser Leu Thr Ile Ser Ser Leu Glu
65                  70                  75                  80

Tyr Glu Asp Met Gly Ile Tyr Tyr Cys Leu Gln Tyr Asp Glu Leu Pro
                85                  90                  95

Phe Thr Phe Gly Ser Gly Thr Lys Leu Glu Ile Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys Ala Ala Ala Leu Glu His His His His
        210                 215                 220

His His
225

<210> SEQ ID NO 4
<211> LENGTH: 235
<212> TYPE: PRT
<213> ORGANISM: Mus musculus

<400> SEQUENCE: 4

Met Asp Ile Lys Met Thr Gln Ser Pro Ser Ser Met Tyr Ala Phe Leu
1               5                   10                  15

Gly Glu Arg Val Thr Ile Thr Cys Lys Ala Ser Gln Asp Ile Asn Ser
                20                  25                  30

Tyr Leu Ser Trp Phe Gln Gln Lys Pro Gly Lys Ser Pro Lys Thr Leu
            35                  40                  45

Ile Tyr Arg Ala Asn Arg Leu Val Asp Gly Val Pro Ser Arg Phe Ser
50                  55                  60

Gly Ser Gly Ser Gly Gln Asp Tyr Ser Leu Thr Ile Ser Ser Leu Glu
65                  70                  75                  80

Tyr Glu Asp Met Gly Ile Tyr Tyr Cys Leu Gln Tyr Asp Glu Leu Pro
                85                  90                  95

Phe Thr Phe Gly Ser Gly Thr Lys Leu Glu Ile Lys Arg Ala Asp Ala
            100                 105                 110

Ala Pro Thr Val Ser Ile Phe Pro Pro Ser Ser Glu Gln Leu Thr Ser
        115                 120                 125
```

```
Gly Gly Ala Ser Val Val Cys Phe Leu Asn Asn Phe Tyr Pro Lys Asp
            130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                    165                 170                 175

Ser Ser Thr Leu Thr Leu Thr Lys Asp Glu Tyr Glu Arg His Asn Ser
                180                 185                 190

Tyr Thr Cys Glu Ala Thr His Lys Thr Ser Thr Ser Pro Ile Val Lys
            195                 200                 205

Ser Phe Asn Arg Asn Glu Cys Ala Ala Ala Arg Ile Ile Ile Arg Arg
210                 215                 220

Ile Arg Arg Ile Glu His His His His His His
225                 230                 235
```

```
<210> SEQ ID NO 5
<211> LENGTH: 243
<212> TYPE: PRT
<213> ORGANISM: Mus musculus

<400> SEQUENCE: 5

Met Ala Ser Gln Val Gln Leu Gln Gln Ser Gly Ala Glu Leu Val Lys
1               5                   10                  15

Pro Gly Ala Ser Val Lys Leu Ser Cys Thr Ala Ser Gly Phe Asn Ile
                20                  25                  30

Lys Asp Tyr Tyr Met His Trp Val Lys Gln Arg Thr Glu Gln Gly Leu
            35                  40                  45

Glu Trp Ile Gly Arg Ile Asp Pro Glu Asp Gly Glu Thr Lys Tyr Ala
        50                  55                  60

Pro Lys Phe Gln Gly Lys Ala Thr Ile Thr Ala Asp Thr Ser Ser Asn
65                  70                  75                  80

Thr Ala Tyr Leu Gln Leu Ser Ser Leu Thr Ser Glu Asp Thr Ala Val
                85                  90                  95

Tyr Tyr Cys Ala Arg Gly Tyr Gly Ser Glu Ala Met Asp Tyr Trp
            100                 105                 110

Gly Gln Gly Thr Ser Leu Thr Val Ser Ser Lys Thr Thr Pro Pro Ser
        115                 120                 125

Val Tyr Pro Leu Ala Pro Gly Ser Ala Ala Gln Thr Asn Ser Met Val
130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Glu Ser Asp Leu Tyr Thr Leu Ser Ser Ser Val Thr Val Pro
            180                 185                 190

Ser Ser Pro Arg Pro Ser Glu Thr Val Thr Cys Asn Val Ala His Pro
        195                 200                 205

Ala Ser Ser Thr Lys Val Asp Lys Lys Ile Pro Arg Asp Cys Gly Ala
210                 215                 220

Ala Ala Arg Ile Ile Ile Arg Arg Ile Arg Arg Ile Glu His His His
225                 230                 235                 240

His His His
```

-continued

```
<210> SEQ ID NO 6
<211> LENGTH: 237
<212> TYPE: PRT
<213> ORGANISM: Mus musculus

<400> SEQUENCE: 6

Met Thr Gly Ser Ile Val Met Thr Gln Ser His Lys Phe Met Ser Thr
1               5                   10                  15

Ser Val Gly Asp Arg Val Ser Ile Thr Cys Lys Ala Ser Gln Asp Val
                20                  25                  30

Asn Thr Ala Val Ala Trp Tyr Gln Gln Lys Pro Gly Gln Ser Pro Lys
            35                  40                  45

Leu Leu Ile Tyr Trp Ala Ser Thr Arg His Thr Gly Val Pro Asp Arg
50                  55                  60

Phe Thr Gly Ser Gly Phe Gly Thr Asp Tyr Thr Leu Thr Ile Ser Ser
65                  70                  75                  80

Val Gln Ala Glu Asp Leu Ala Leu Tyr Tyr Cys Gln Gln His Tyr Ser
                85                  90                  95

Thr Pro Trp Thr Phe Gly Gly Gly Thr Lys Leu Glu Ile Lys Arg Ala
            100                 105                 110

Asp Ala Ala Pro Thr Val Ser Ile Phe Pro Pro Ser Ser Glu Gln Leu
        115                 120                 125

Thr Ser Gly Gly Ala Ser Val Val Cys Phe Leu Asn Asn Phe Tyr Pro
130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys Ala Ala Ala Arg Ile Ile Ile
    210                 215                 220

Arg Arg Ile Arg Arg Ile Glu His His His His His His
225                 230                 235

<210> SEQ ID NO 7
<211> LENGTH: 241
<212> TYPE: PRT
<213> ORGANISM: Homo sapiens

<400> SEQUENCE: 7

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Ser
                20                  25                  30

Tyr Ala Met Ser Trp Val Arg Gln Ala Pro Gly Lys Gly Leu Glu Trp
            35                  40                  45

Val Ser Ala Ile Ser Gly Ser Gly Gly Ser Thr Tyr Tyr Ala Asp Ser
50                  55                  60

Val Lys Gly Arg Phe Thr Ile Ser Arg Asp Asn Ser Lys Asn Thr Leu
65                  70                  75                  80
```

```
Tyr Leu Gln Met Asn Ser Leu Arg Ala Glu Asp Thr Ala Val Tyr Tyr
                85                  90                  95

Cys Ala Lys Pro Phe Pro Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Gly Ala Ala Ala
    210                 215                 220

Arg Ile Ile Ile Arg Ile Arg Ile Glu His His His His
225                 230                 235                 240

His

<210> SEQ ID NO 8
<211> LENGTH: 237
<212> TYPE: PRT
<213> ORGANISM: Homo sapiens

<400> SEQUENCE: 8

Met Glu Ile Val Leu Thr Gln Ser Pro Gly Thr Leu Ser Leu Ser Pro
1               5                   10                  15

Gly Glu Arg Ala Thr Leu Ser Cys Arg Ala Ser Gln Ser Val Ser Ser
            20                  25                  30

Ser Tyr Leu Ala Trp Tyr Gln Gln Lys Pro Gly Gln Ala Pro Arg Leu
        35                  40                  45

Leu Ile Tyr Gly Ala Ser Ser Arg Ala Thr Gly Ile Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Gln Gln Thr Gly Arg Ile
                85                  90                  95

Pro Pro Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205
```

Lys Ser Phe Asn Arg Gly Glu Cys Gly Ala Ala Arg Ile Ile Ile
210                 215                 220

Arg Arg Ile Arg Arg Ile Glu His His His His His
225                 230                 235

<210> SEQ ID NO 9
<211> LENGTH: 241
<212> TYPE: PRT
<213> ORGANISM: Homo sapiens

<400> SEQUENCE: 9

Met Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Ser
                20                  25                  30

Phe Ser Met Ser Trp Val Arg Gln Ala Pro Gly Lys Gly Leu Glu Trp
            35                  40                  45

Val Ser Ser Ile Ser Gly Ser Ser Gly Thr Thr Tyr Tyr Ala Asp Ser
50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Pro Phe Pro Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Gly Ala Ala Ala
    210                 215                 220

Arg Ile Ile Ile Arg Arg Ile Arg Arg Ile Glu His His His His
225                 230                 235                 240

His

<210> SEQ ID NO 10
<211> LENGTH: 237
<212> TYPE: PRT
<213> ORGANISM: Homo sapiens

<400> SEQUENCE: 10

Met Glu Ile Val Leu Thr Gln Ser Pro Gly Thr Leu Ser Leu Ser Pro
1               5                   10                  15

Gly Glu Arg Ala Thr Leu Ser Cys Arg Ala Ser Gln Ser Val Ser Ser
                20                  25                  30

Ser Tyr Leu Ala Trp Tyr Gln Gln Lys Pro Gly Gln Ala Pro Arg Leu
            35                  40                  45

-continued

```
Leu Ile Tyr Gly Ala Ser Ser Arg Ala Thr Gly Ile Pro Asp Arg Phe
 50                  55                  60

Ser Gly Ser Gly Ser Gly Thr Asp Phe Thr Leu Thr Ile Ser Arg Leu
 65                  70                  75                  80

Glu Pro Glu Asp Phe Ala Val Tyr Tyr Cys Gln Gln Thr Gly Arg Ile
                 85                  90                  95

Pro Pro Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Gly Ala Ala Arg Ile Ile Ile
210                 215                 220

Arg Arg Ile Arg Arg Ile Glu His His His His His His
225                 230                 235

<210> SEQ ID NO 11
<211> LENGTH: 9
<212> TYPE: PRT
<213> ORGANISM: Artificial Sequence
<220> FEATURE:
<223> OTHER INFORMATION: Polystyrene binding sequence
<220> FEATURE:
<221> NAME/KEY: MISC_FEATURE
<222> LOCATION: (2)..(7)
<223> OTHER INFORMATION: X is Ile, Leu, Val, Ala, Gly, Met, Ser or Thr

<400> SEQUENCE: 11

Arg Xaa Xaa Xaa Arg Arg Xaa Arg Arg
 1               5

<210> SEQ ID NO 12
<211> LENGTH: 16
<212> TYPE: PRT
<213> ORGANISM: Escherichia coli

<400> SEQUENCE: 12

Gly Asp Ser Asp Glu Trp Thr Phe Gly Ala Gln Met Glu Ile Trp Trp
 1               5                  10                  15

<210> SEQ ID NO 13
<211> LENGTH: 20
<212> TYPE: PRT
<213> ORGANISM: Escherichia coli

<400> SEQUENCE: 13

Trp Thr Pro Ile Met Ser Thr Val Met Glu Ile Gly Tyr Asp Asn Val
 1               5                  10                  15

Glu Ser Gln Arg
            20
```

```
<210> SEQ ID NO 14
<211> LENGTH: 20
<212> TYPE: PRT
<213> ORGANISM: Escherichia coli

<400> SEQUENCE: 14

Asn Ser Asn Phe Phe Gly Leu Val Asp Gly Leu Asn Phe Ala Val Gln
1               5                   10                  15

Tyr Leu Gly Lys
            20

<210> SEQ ID NO 15
<211> LENGTH: 24
<212> TYPE: PRT
<213> ORGANISM: Escherichia coli

<400> SEQUENCE: 15

Thr Gln Asp Val Leu Leu Val Ala Gln Tyr Gln Phe Asp Phe Gly Leu
1               5                   10                  15

Arg Pro Ser Ile Ala Tyr Thr Lys
            20

<210> SEQ ID NO 16
<211> LENGTH: 24
<212> TYPE: PRT
<213> ORGANISM: Escherichia coli

<400> SEQUENCE: 16

Asn Ile Leu Ala Val Ile Val Pro Ala Leu Leu Val Ala Gly Thr Ala
1               5                   10                  15

Asn Ala Ala Glu Ile Tyr Asn Lys
            20

<210> SEQ ID NO 17
<211> LENGTH: 13
<212> TYPE: PRT
<213> ORGANISM: Escherichia coli

<400> SEQUENCE: 17

Gln Val Gly Val Pro Tyr Ile Ile Val Phe Leu Asn Lys
1               5                   10

<210> SEQ ID NO 18
<211> LENGTH: 28
<212> TYPE: PRT
<213> ORGANISM: Escherichia coli

<400> SEQUENCE: 18

Ser Asn Gly Asp Gly Val Gly Gly Ser Ile Ser Tyr Glu Tyr Glu Gly
1               5                   10                  15

Phe Gly Ile Val Gly Ala Tyr Gly Ala Ala Asp Arg
            20                  25

<210> SEQ ID NO 19
<211> LENGTH: 24
<212> TYPE: PRT
<213> ORGANISM: Escherichia coli
```

```
<400> SEQUENCE: 19

Asp Val Glu Gly Ile Gly Asp Val Asp Leu Val Asn Tyr Phe Glu Val
1               5                  10                  15

Gly Ala Thr Tyr Tyr Phe Asn Lys
            20
```

ANTIBODY-IMMOBILIZED CARRIER, METHOD OF PRODUCING ANTIBODY-IMMOBILIZED CARRIER, AND USE OF SAID ANTIBODY-IMMOBILIZED CARRIER

CROSS REFERENCE TO RELATED APPLICATIONS

The present application is a Section 371 U.S. national stage entry of pending International Patent Application No. PCT/JP2011/053157, International Filing Date Feb. 15, 2011, which published on Aug. 25, 2011 as Publication No. WO 2011/102342, which claims the benefit of Japanese Patent Application No. 2010-031684, filed Feb. 16, 2010, the contents of which are incorporated by reference in their entireties.

TECHNICAL FIELD

The present invention relates to an antibody-immobilized carrier, particularly to a carrier onto which lower molecular weight antibodies are immobilized, a method of producing the antibody-immobilized carrier, and use of the antibody-immobilized carrier.

BACKGROUND ART

Conventionally, immunoassay in which a trace substance is detected by utilizing antigen-antibody reaction has been known. Moreover, recently, antibody medicines utilizing functions of antibodies have been actively developed. Such antibody medicines have excellent effects and less adverse effects, and act on various drug targets. Moreover, the antibody medicines can be industrially produced. Accordingly, the antibody medicines are drawing attentions, as a technology that allows quickly providing a treatment against target molecules found in genome researches. The antibody medicines have various functions of, for example, a blocking antibody that is combined to a receptor or a ligand and inhibiting signaling, a signaling antibody that is combined to a receptor and shows a receptor crosslinking effect, and a targeting antibody having ADCC activity or CDC activity and therefore having cytotoxicity.

Development of such antibody medicines generally starts with gene search followed by identification of an antigen that becomes a target of an antibody medicine, preparation of an antibody that binds specifically to the antigen, check of a pharmacological effect of the antibody, and ultimate mass production of the antibody medicine. In this development flow, a process of screening an antibody that binds specifically to an antigen is considered important.

As a technique for screening antibodies, a method employing phage display is known. This method is a technique in which: first, an antibody library presenting various antigen-specific antibodies on phages is prepared; and then, screening of antibodies that binds specifically to a specific antigen is carried out (See Patent Literature 1, for example).

CITATION LIST

Patent Literature

Patent Literature 1
Publication of Japanese Translation of PCT International Application, Tokuhyou, No. 2009-511892 A (Publication Date: Mar. 19, 2009)

SUMMARY OF INVENTION

Technical Problem

However, an antibody screening method utilizing the phage display described above is not sufficient. This is because: (a) work operation is complicated; (b) isolation of a positive clone is difficult; and (c) moreover, false positive clones may be selected. Therefore, development of a novel technique, other than the phage display, that can be used in antibody screening has been strongly desired.

The present invention is attained in view of the above problems. An object of the present invention is to provide an antibody-immobilized carrier which can be used in antibody screening, a method of producing the antibody-immobilized carrier, and use of antibody-immobilized carrier.

Solution to Problem

As a result of diligent studies for achieving the object above, the inventors of the present invention developed an innovative technique that made it possible to carry out effective screening of an antibody recognizing a specific antigen. In this technique, first, heavy chains and light chains derived from different antibodies are made into smaller molecules, and then a number of combinations of the smaller molecules are immobilized onto a carrier. As a result, the inventors accomplished the present invention. In other words, the present invention is configured as follows:

(1) An antibody-immobilized carrier including at least one antibody immobilized region where a heavy-chain low-molecular-weight antibody and a light-chain low-molecular-weight antibody are separately immobilized, the at least one antibody immobilized region being included in an independent manner, the heavy-chain low-molecular-weight antibody including a heavy-chain variable region, the light-chain low-molecular-weight antibody including a light-chain variable region, the heavy-chain low-molecular-weight antibody and the light-chain low-molecular-weight antibody each being derived from an antibody recognizing a different antigen.

(2) The antibody-immobilized carrier as set forth in (1), wherein: each of the heavy-chain low-molecular-weight antibody and the light-chain low-molecular-weight antibody is separately immobilized onto a carrier via a carrier binding peptide that binds to a material of a carrier surface; and the carrier binding peptide is provided to a C-terminus side of the heavy-chain variable region in the heavy-chain low-molecular-weight antibody or to a C-terminus side of the light-chain variable region in the light-chain low-molecular-weight antibody.

(3) The antibody-immobilized carrier as set forth in (2), wherein: the material of the carrier surface is plastic resin having been hydrophilized by property modification, the plastic resin being polystyrene, polycarbonate, polypropylene, polyethylene, polydimethylsiloxane (PDMS) or polymethyl methacrylate (PMMA).

(4) The antibody-immobilized carrier as set forth in (2) or (3), wherein: the carrier binding peptide is a peptide that binds to hydrophilic polystyrene, hydrophilic polycarbonate, hydrophilic polypropylene, hydrophilic polyethylene, hydrophilic polydimethylsiloxane (PDMS) or hydrophilic polymethyl methacrylate (PMMA).

(5) The antibody-immobilized carrier as set forth in any one of (1) to (4), wherein: the heavy-chain low-molecular-weight antibody is a heavy-chain low-molecular-weight antibody consisting of the heavy-chain variable region or a heavy-chain low-molecular-weight antibody (Fab H) consisting of a heavy-chain variable region and a first heavy-chain constant region ($CH_1$).

(6) The antibody-immobilized carrier as set forth in any one of (1) to (5), wherein: the light-chain low-molecular-weight antibody is a light-chain low-molecular-weight antibody consisting of the light-chain variable region or a light-chain low-molecular-weight antibody (Fab L) consisting of a light-chain variable region and a light-chain constant region ($C_k$).

(7) A method of producing an antibody-immobilized carrier including the step of: immobilizing a heavy-chain low-molecular-weight antibody including a heavy-chain variable region and a light-chain low-molecular-weight antibody including a light-chain variable region separately onto a carrier, so that an antibody immobilized region is prepared, the heavy-chain low-molecular-weight antibody and the light-chain low-molecular-weight antibody each being derived from an antibody recognizing a different antigen.

(8) The method as set forth in (7), wherein the step of immobilizing is repeated at least two times so that two or more of the antibody immobilized region are provided in an independent manner.

(9) The method as set forth in (7), wherein the step of immobilizing including: (a) the first sub-step of immobilizing, onto the carrier, insoluble aggregates of the heavy-chain low-molecular-weight antibody and the light-chain low-molecular-weight antibody by putting the denatured aggregates in contact with a carrier surface, the denatured insoluble aggregates each having been denatured by a denaturing agent and being in a denatured state; and (b) the second sub-step of refolding the heavy-chain low-molecular-weight antibody and the light-chain low-molecular-weight antibody each in the denatured state, by removing the denaturing agent from the heavy-chain low-molecular-weight antibody and the light-chain low-molecular-weight antibody that are in the denatured state and immobilized.

(10) The method as set forth in (9), wherein the first sub-step and the second sub-step in the step of immobilizing are carried out, separately for each of the heavy-chain low-molecular-weight antibody and the light-chain low-molecular-weight antibody.

(11) The method as set forth in (10), wherein: in the step of immobilizing, after the first sub-step and the second sub-step are carried out for the light-chain low-molecular-weight antibody, the first sub-step and the second sub-step are carried out for the heavy-chain low-molecular-weight antibody.

(12) The method as set forth in any one of (9) to (11), wherein: the first sub-step employs, as the denaturing agent, urea whose concentration is in a range of 0.5 M to 4M.

(13) The antibody-immobilized carrier obtained by the method as set forth in any one of (8) to (12) above.

(14) An antibody screening method including the step of: screening a heavy-chain low-molecular-weight antibody and/or a light-chain low-molecular-weight antibody each recognizing a specific antigen, by using the antibody-immobilized carrier as set forth in any one of (1) to (6) and (13) above.

(15) A method of screening a human antibody recognizing a specific antigen by using the antibody-immobilized carrier as set forth in any one of (1) to (6), and (13) above, the screening being carried out by using a chimeric antibody or a humanized antibody each recognizing the specific antigen, the heavy-chain low-molecular-weight antibody being immobilized onto the at least one antibody immobilized region and including a heavy-chain variable region derived from the chimeric antibody or the humanized antibody, the light-chain low-molecular-weight antibody being a light-chain low-molecular-weight antibody that is immobilized onto the at least one antibody immobilized region and that includes a light-chain variable region derived from a random human antibody, the method including the steps of: (i) putting the specific antigen in contact with the antibody-immobilized carrier; (ii) detecting an antibody immobilized region recognizing the specific antigen on the antibody-immobilized carrier; and (iii) determining a light-chain low-molecular-weight antibody immobilized on the antibody immobilized region detected in the step (ii), as a candidate for a light-chain variable region of the human antibody recognizing the specific antigen.

(16) The method of screening as set forth in (15), further including the steps of: (iv) putting the specific antigen in contact with another antibody-immobilized carrier including another antibody immobilized region onto which (a) the light-chain low-molecular-weight antibody determined as the candidate in the step (iii) and (b) a heavy-chain low-molecular-weight antibody including a heavy-chain variable region derived from a random human antibody are immobilized; (v) detecting an antibody immobilized region recognizing the specific antibody on the another antibody-immobilized carrier; and (vi) determining a heavy-chain low-molecular-weight antibody immobilized onto the antibody immobilized region detected in the step (v), as a candidate for a heavy-chain variable region of the human antibody recognizing the specific antigen.

(17) A method of screening a human antibody recognizing a specific antigen by using the antibody-immobilized carrier as set forth in any one of (1) to (6), and (13) above, the screening being carried out by using a chimeric antibody or a humanized antibody each recognizing the specific antigen, the light-chain low-molecular-weight antibody being immobilized onto the at least one antibody immobilized region and including a light-chain variable region derived from the chimeric antibody or the humanized antibody, the heavy-chain low-molecular-weight antibody being a heavy-chain low-molecular-weight antibody that is immobilized onto the at least one antibody immobilized region and that includes a heavy-chain variable region derived from a random human antibody, the method including the steps of: (i) putting the specific antigen in contact with the antibody-immobilized carrier; (ii) detecting an antibody immobilized region recognizing the specific antigen on the antibody-immobilized carrier; and (iii) determining a heavy-chain low-molecular-weight antibody immobilized on the antibody immobilized region detected in the step (ii), as a candidate for a heavy chain variable region of the human antibody recognizing the specific antigen.

(18) The method of screening as set forth in (17), further including the steps of: (iv) putting the specific antigen in contact with another antibody-immobilized carrier including another antibody immobilized region onto which (a) the heavy-chain low-molecular-weight antibody determined as the candidate in the step (iii) and (b) a light-chain low-molecular-weight antibody including a light-chain variable region derived from a random human antibody are immobilized; (v) detecting an antibody immobilized region recognizing the specific antibody on the another antibody-immobilized carrier; and (vi) determining a light-chain low-molecular-weight antibody immobilized onto the antibody immobilized region detected in the step (v), as a candidate for a light-chain variable region of the human antibody recognizing the specific antigen.

(19) A method of producing a human antibody, the method including the step of producing the human antibody by combining the candidate for the light-chain variable region of the human antibody and the candidate for the heavy-chain variable region of the human antibody, the candidate for the light-chain variable region and the candidate for the heavy-chain variable region being determined by the method of screening as set forth in any one of (15) to (18) above.

Advantageous Effects of Invention

Because the antibody-immobilized carrier of the present invention is a carrier onto which a number of combinations of a heavy chain and a light chain each derived from a different antibody are immobilized, screening of antibodies recognizing a specific antigen can be efficiently carried out. The antibody-immobilized carrier is applicable not only to the above but also to screening of antibodies for diagnosis. Further, antibody-immobilized carrier is also applicable to various immunoassays utilizing antigen-antibody reaction.

For a fuller understanding of the nature and advantages of the invention, reference should be made to the ensuing detailed description taken in conjunction with the accompanying drawings.

BRIEF DESCRIPTION OF DRAWINGS (a) of FIG. 1 is a diagram schematically showing a state where a set of a heavy-chain low-molecular-weight antibody and a light-chain low-molecular-weight antibody each immobilized onto a carrier reacts with an antigen; and (b) of FIG. 1 is a diagram schematically showing a configuration of an antibody-immobilized carrier onto which a number of combinations of a heavy-chain low-molecular-weight antibody and a light-chain low-molecular-weight antibody are immobilized.

FIG. 2 is a diagram showing a result of examination on antigen binding activity by using a carrier prepared by immobilizing thereon one or a combination of the following low-molecular-weight antibodies derived from mouse anti-RNase antibody: Fab H, Fab L, a low-molecular-weight antibody in which PS-tag is bound to Fab H, and a low-molecular-weight antibody in which PS-tag is bound to Fab L.

FIG. 3 is a diagram showing a result of examination on conditions for solid phase refolding by using a carrier prepared by immobilizing thereon one or a combination of the following low-molecular-weight antibodies derived from mouse anti-RNase antibody: Fab H, Fab L, a low-molecular-weight antibody in which PS-tag is bound to Fab H, and a low-molecular-weight antibody in which PS-tag is bound to Fab L.

FIG. 4 is a diagram showing a result of detecting mouse RNase as an antigen by using a carrier prepared by immobilizing thereon one or a combination of the following low-molecular-weight antibodies derived from a mouse anti-CRP antibody, a mouse anti-RNase antibody, a human anti-IFNG antibody, and a human anti-ED-B antibody: (a) low-molecular-weight antibodies in each of which PS-tag is bound to Fab H; and (b) low-molecular-weight antibodies in each of which PS-tag is bound to Fab L.

FIG. 5 is a diagram showing a result of detecting mouse CRP as an antigen by using a carrier prepared by immobilizing thereon one or a combination of the following low-molecular-weight antibodies derived from a mouse anti-CRP antibody, a mouse anti-RNase antibody, a human anti-IFNG antibody, and a human anti-ED-B antibody: (a) low-molecular-weight antibodies in each of which PS-tag is bound to Fab H; and (b) low-molecular-weight antibodies in each of which PS-tag is bound to Fab L.

FIG. 6 is a diagram showing a result of detecting human ED-B as an antigen by using a carrier prepared by immobilizing thereon one or a combination of the following low-molecular-weight antibodies derived from a mouse anti-CRP antibody, a mouse anti-RNase antibody, a human anti-IFNG antibody, and a human anti-ED-B antibody: (a) low-molecular-weight antibodies in each of which PS-tag is bound to Fab H; and (b) low-molecular-weight antibodies in each of which PS-tag is bound to Fab L.

FIG. 7 is a diagram showing a result of detecting human IFNG as an antigen by using a carrier prepared by immobilizing thereon one or a combination of the following low-molecular-weight antibodies derived from a mouse anti-CRP antibody, a mouse anti-RNase antibody, a human anti-IFNG antibody, and a human anti-ED-B antibody: (a) low-molecular-weight antibodies in each of which PS-tag is bound to Fab H; and (b) low-molecular-weight antibodies in each of which PS-tag is bound to Fab L.

FIG. 8 is a diagram showing a result of examination on difference in antigen binding activity caused by difference in immobilization method, by using carriers carrier each prepared by immobilizing thereon one or a combination of the following low-molecular-weight antibodies derived from mouse anti-RNase antibody: Fab H, Fab L, a low-molecular-weight antibody in which PS-tag is bound to Fab H, and a low-molecular-weight antibody in which PS-tag is bound to Fab L.

DESCRIPTION OF EMBODIMENTS

Figure 1:
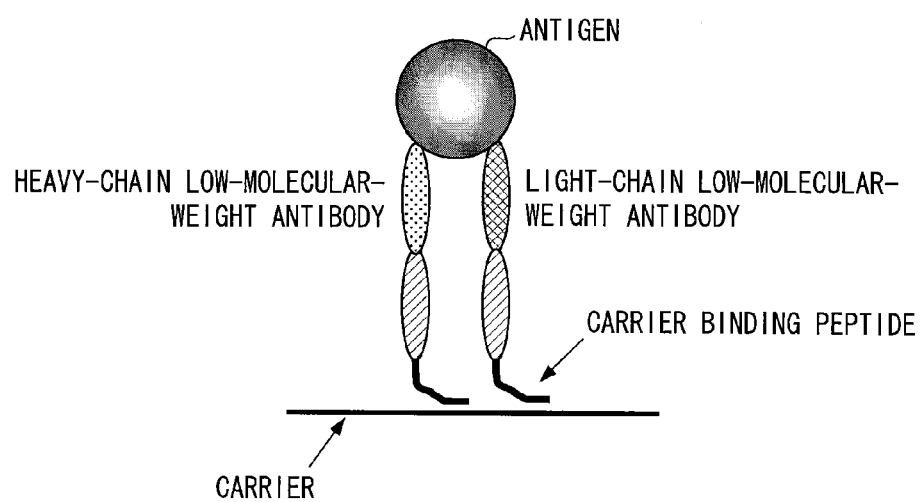
Figure 1:
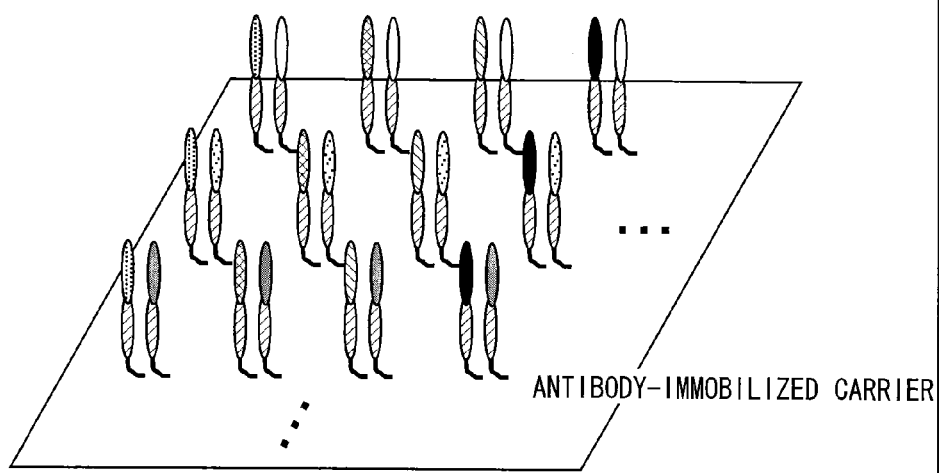

One embodiment of the present invention is described below. Note that all professional literatures and patent literatures cited in the present specification are incorporated herein as references in the present specification. In the present specification, unless specifically noted, "A to B" indicating a range of numerical values means "A or more (i.e., containing A and greater than A) and B or less (i.e., containing B and less than B). The wordings of all of "recognize an antigen", "have affinity for an antigen" and "bind to an antigen" mean that an antibody component immunologically reacts with an antigen. The above wordings are synonyms and interchangeable with each other.

<1. Antibody-Immobilized Carrier>

An antibody-immobilized carrier of the present invention only needs to include at least one antibody immobilized region where a heavy-chain low-molecular-weight antibody and a light-chain low-molecular-weight antibody are separately immobilized, the at least one antibody immobilized region being included in an independent manner, the heavy-chain low-molecular-weight antibody including at least a heavy-chain variable region, the light-chain low-molecular-weight antibody including at least a light-chain variable region, the heavy-chain low-molecular-weight antibody and the light-chain low-molecular-weight antibody each being derived from an antibody recognizing a different antigen. The antibody-immobilized carrier is not specifically limited in regard to other configurations such as concrete structures, materials, and forms.

The "low-molecular-weight antibody" as used in the present specification is an antibody fragment of a whole antibody (e.g., whole IgG) from which a part is deficient and includes at least a heavy-chain variable region (VH) or light-chain variable region (VL). The "low-molecular-weight antibody" only needs to have an ability to bind to an antigen. Specifically preferable examples of the low-molecular-weight antibody are VH, VL, and Fab, Fab', and F(ab')2 in a heavy chain or a light chain. In particular, the heavy-chain low-molecular-weight antibody is preferably a heavy-chain low-molecular-weight antibody consisting of (a) a heavy-chain variable region or (b) Fab H: a heavy-chain variable region and a first heavy-chain constant region ($CH_1$). Meanwhile, particularly, the light-chain low-molecular-weight antibody is preferably a light-chain low-molecular-weight antibody consisting of (a) a light-chain variable region or (b) Fab L: a light-chain variable region and a light-chain constant region ($C_k$). The above low-molecular-weight antibodies are preferable because these low-molecular-weight antibodies can be efficiently immobilized to a carrier.

For obtaining such a low-molecular-weight antibody, a conventionally known cloning technique or a conventionally known chemical synthesis method can be used in production. For example, by employing the cloning technique, it is possible to collect a peptide having the amino acid sequence of the low-molecular-weight antibody by (i) first, preparing DNA encoding the antibody fragment (low-molecular-weight antibody), (ii) obtaining recombinant DNA, by inserting thus prepared DNA into an autonomously replicating vector, (iii) introducing as appropriate thus obtained recombinant DNA into a host such as *E. coli, Bacillus subtilis*, mycobacterium, yeast, filamentous fungi, a plant cell, an insect cell, an animal cell or the like and thereby obtaining a transformant, and (iv) culturing the transformant and collecting the peptide from thus cultured material (See, for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; and Bird, R. E. and Walker, B. W., Trends Biotechnol. (1991) 9, 132-137).

Alternatively, the low-molecular-weight antibody can be obtained by (i) preparing DNA encoding the low-molecular-weight antibody and (ii) synthesizing in an acellular protein synthesis system by using cell extract liquid of wheat germ or *E. coli*, or the like. As another alternative, the low-molecular-weight antibody can also be obtained by successively performing dehydration synthesis and extension of an amino acid with use of a common peptide chemical synthesis method such as a "solid-phase synthesis method" or a "liquid-phase synthesis method".

In particular, an antibody production technique employing gene recombination makes it possible to mass produce antibodies at low cost. Therefore, preferably the low-molecular-weight antibodies each having, as a basic skeleton, a variable region that binds to an antigen, are produced by (i) first isolating an antibody producing gene from a general antibody producing cell strain, (ii) then preparing, from the antibody producing gene, a nucleotide sequence corresponding to the low-molecular-weight antibody, and (iii) subsequently incorporating the nucleotide sequence into *E. coli* or the like.

The following provides an example of a method of producing the low-molecular-weight antibody. First, from a hybridoma that produces an antibody, mRNA or total RNA encoding a variable region is isolated. Here, mRNA or total RNA may be isolated by a known method such as guanidine ultracentrifugation (Chirgwin, J. M. et al., Biochemistry (1979) 18, 5294-5299), a guanidine thiocyanate hot phenol method, a guanidine thiocyanate-guanidine hydrochloride method, a guanidine thiocyanate cesium chloride method, alkali sucrose gradient centrifugation, or an AGPC method (Chomczynski, P. et al., Anal. Biochem. (1987) 162, 156-159). Thereby, total RNA is prepared. Then, by using mRNA Purification Kit (manufactured by Pharmacia Corporation) or the like, target mRNA is prepared. Alternatively, by using Quick-Prep mRNA Purification Kit (manufactured by Pharmacia Corporation) or the like, mRNA may be directly prepared.

By using a reverse transcriptase from thus obtained mRNA, cDNA of an antibody variable region is synthesized. The synthesis of cDNA is carried out by using AMV Reverse Transcriptase First-strand cDNA Synthesis Kit (manufactured by Seikagaku Corporation) or the like. Further, for synthesis and amplification of cDNA, 5'-AmpliFINDER RACE Kit (manufactured by Clontech) and 5'-RACE (Frohman, M. A. et al., Proc. Natl. Acad. Sci. USA (1988) 85, 8998-9002, Belyaysky, A. et al., Nucleic Acids Res. (1989) 17, 2919-2932) utilizing PCR can be used.

From a PCR product obtained as described above, a target DNA fragment is purified and joined to vector DNA. Further, a recombinant vector is prepared by using the vector DNA. Moreover, a desired recombinant vector is prepared by introducing thus obtained recombinant vector into *E. coli* or the like and selecting a colony. Furthermore, a target DNA sequence is checked by a conventionally known method such as a dideoxynucleotide chain termination method. The antibody of the present invention obtained as described above may be expressed by a conventionally known method and obtained.

In the case where *E. coli* is used, an antibody gene to be expressed may be expressed by functionally binding the antibody gene to a downstream of a common useful promoter. Examples of such a promoter are lacz promoter and araB promoter. In a case where lacz promoter is used, the antibody gene can be expressed by a method of Ward et al. (Nature (1098) 341, 544-546; FASEB J. (1992) 6, 2422-2427). Meanwhile, in a case where araB promoter is used, the antibody gene can be expressed by a method of Better et al. (Science (1988) 240, 1041-1043). Thus produced antibody aggregates in a cytoplasm and forms an inclusion body. However, thus produced antibody may be used by appropriately refolding a structure of the antibody, after an antibody protein aggregate is isolated.

Note that a signal sequence for antibody secretion may be inserted between the promoter and the antigen gene so that the antibody may be secreted into periplasm. This method is conventionally known to a person skilled in the art. As the signal sequence for antibody secretion, pelB signal sequence (Lei, S. P. et al J. Bacteriol. (1987) 169, 4379) may be used in a case where the antibody is to be produced in a periplasm of *E. coli*. After the antibody produced in the periplasm is isolated, a structure of the antibody is appropriately refolded and then the antibody is used.

An origin of replication here may be derived from SV40, polyoma virus, adenovirus, bovine papillomavirus (BPV), or the like. Further, for amplifying the number of gene copies in a host cell system, the expression vector may include, as a selection marker, aminoglycoside transferase (APH) gene, thimidine kinase (TK) gene, *E. coli* xanthine-guanine phosphoribosyl transferase (Ecogpt) gene, dihydrofolate reductase (dhfr) gene or the like.

For production of the antibody used in the present invention, any expression system such as eucaryotic cells or procaryotic cells may be used. Examples of the eucaryotic cells may be animal cells such as established mammalian cell lines, insect cell lines, filamentous fungal cells, and yeast cells. Examples of the procaryotic cells are bacterial cells such as *E. coli* cells.

Next, thus transformed host cell is cultured in vitro or in vivo, so that a target antibody is produced. The transformed host cell may be cultured by a conventionally known method. For example, as a culture fluid, DMEM, MEM, RPMI1640, or IMDM may be used and at the same time, serum replenisher fluid such as fetal calf serum (FCS) may be used.

Further, the antibody expressed and produced as described above may be purified so as to be uniform. A method for the purification of the low-molecular-weight antibody may be a conventionally known method and not specifically limited. For example, the isolation and purification of the low-molecular-weight antibody to be used in the present invention may be carried by using an affinity column. As such an affinity column, for example, there are Hyper D, POROS, and Sepharose F.F. (manufactured by Pharmacia Corporation) as a column employing a protein A column. Other than this, the method may be a general isolation and purification method generally used for proteins and is limited by no means. For example, the antibody can be isolated and purified by, other than the affinity column, one or a combination of two or more selected as appropriate from among a chromatography column, a filter, ultrafiltration, salt precipitation, dialysis and the like (Antibodies A Laboratory Manual. Ed Harlow, David Lane, Cold Spring Harbor Laboratory, 1988).

Further, as described later, in the present invention, the low-molecular-weight antibody has a carrier binding peptide as a tag. Therefore, by putting solution containing a product from the transformant in contact with a carrier surface, the low-molecular-weight antibody can be directly adsorbed onto the carrier surface and thereby isolated and purified. The solution containing the product is any solution which contains a target low-molecular-weight antibody and in which an unnecessary impurity from the host is present. Such solution encompasses, for example, disrupted bacterial cell solution, a soluble fraction obtained by centrifugation of disrupted bacterial cell solution, a material obtained by solubilizing an insoluble fraction obtained by centrifugation of disrupted bacterial cell solution, a cell membrane fraction, a cell wall fraction, a secretion produced and secreted from a cell, body fluid, or incompletely purified materials thereof.

Further, in a case where a large amount of heterogeneous genes are expressed in a host by introducing recombinant DNA, the low-molecular-weight antibody may be produced as an insoluble aggregate (inclusion body) for preventing an adverse effect onto the host due to protein produced. Even in a case where the low-molecular-weight antibody is produced as an insoluble aggregate, the insoluble aggregate may be solubilized by a denaturing agent and then directly immobilized onto the carrier surface. Furthermore, in some cases, by removing the denaturing agent from thus solubilized aggregate immobilized onto the carrier surface, the low-molecular-weight antibody may be refolded.

Further, even in a case where a low-molecular-weight antibody has a tertiary structure somehow denatured other than the case of the insoluble aggregate, the low-molecular-weight antibody structure can be directly immobilized onto the carrier surface as long as this low-molecular-weight antibody structure is the low-molecular-weight antibody of the present invention. Further, the low-molecular-weight antibody may be refolded by providing an appropriate refolding buffer to the low-molecular-weight antibody in an immobilized state. As causes of the above denaturization, there are physical causes such as heating, freezing, high pressure, supersonic wave, ultraviolet ray, X-ray, stirring, adsorption, and dilution, and chemical causes such as extreme acidity or alkalinity, organic solvents, heavy metal salts, denaturing agents, and surfactants. Note that the method for obtaining the low-molecular-weight antibody described above is applicable not only in a case where the low-molecular-weight antibody is obtained but also in a case where an antibody described later, for example, a whole human antibody, is obtained. In such a case, the above explanation can be referred to as appropriate.

Further, the antibody immobilized carrier only needs to be provided with at least one antibody immobilized region, and the number of the at least one antibody immobilized region is not specifically limited. More preferably, two or more of the antibody immobilized region are provided in an independent manner.

The wording "two or more . . . are provided in an independent manner" means that a set of the heavy-chain low-molecular-weight antibody and the light-chain low-molecular-weight antibody are immobilized in one antibody immobilized region and two or more of such an antibody immobilized region are independently present on the carrier. Further, "the heavy-chain low-molecular-weight antibody and the light-chain low-molecular-weight antibody each is derived from an antibody recognizing a different antigen". This means that each of the heavy-chain low-molecular-weight antibody and the light-chain low-molecular-weight antibody is prepared from an antibody that has affinity for a different antigen. For example, there may be an exemplary case where the heavy-chain low-molecular-weight antibody is derived from an anti-interferon γ (IFNG) antibody and the light-chain low-molecular-weight antibody is derived from an anti-interleukin 6 receptor (IL-6R) antibody. Further, an organism from which the antibody is originally derived is preferably a human. However, the organism is not limited to a human but the antibody may be derived from any of various vertebrates such as chickens, mice, rats, rabbits, sheep, and monkeys.

The carrier in the present invention may be any carrier as long as an antibody can be immobilized to the carrier. Generally, the carrier is insoluble in water. The carrier may be made of a film, a bead, a gel or a substrate of a material selected from resin, nylon, nitrocellulose, polysaccharide, glass and metal. The carrier is on a support made of glass, ceramics, metal, plastic, or the like, as needed.

(a) and (b) of FIG. 1 schematically show one example of a structure of the antibody-immobilized carrier of the present invention. (a) of FIG. 1 is a diagram schematically showing a state where a set of a heavy-chain low-molecular-weight antibody and a light-chain low-molecular-weight antibody each immobilized onto a carrier reacts with an antigen; and (b) of FIG. 1 is a diagram schematically showing a state in which a number of combinations of a heavy-chain low-molecular-weight antibody and a light-chain low-molecular-weight antibody are immobilized.

In the antibody-immobilized carrier of the present invention, as shown in (a) and (b) of FIG. 1, each of the heavy-chain low-molecular-weight antibody and the light-chain low-molecular-weight antibody is separately immobilized onto the carrier via a carrier binding peptide. In other words, the heavy-chain low-molecular-weight antibody and the light-chain low-molecular-weight antibody form a pair in one antibody immobilized region, and each of the heavy-chain low-molecular-weight antibody and the light-chain low-molecular-weight antibody is independently immobilized as a separate molecule in the one antibody immobilized region. Note that the heavy-chain low-molecular-weight antibody and the light-chain low-molecular-weight antibody only need to be separately immobilized at immobilization in the antibody immobilized region. After the immobilization in the antibody immobilized region, the heavy-chain low-molecular-weight antibody and the light-chain low-molecular-weight antibody may be interact with each other or form S—S bond or the like.

Each of the heavy-chain low-molecular-weight antibody and the light-chain low-molecular-weight antibody is immobilized onto the carrier via the "carrier binding peptide". At the immobilization of the low-molecular-weight antibody, each of the low-molecular-weight antibody is preferably immobilized in a form in which: C-terminus side is bound to the carrier surface at a right angle with respect to the carrier surface; an antigen binding site is facing outward; and the antibody is sterically in a normal position. This is for allowing each of the heavy-chain variable region and the light-chain variable region to contribute to antigen-antibody reaction. Therefore, preferably, the "carrier binding peptide" is provided to C-terminus side of the heavy-chain variable region in the heavy-chain low-molecular-weight antibody while the "carrier binding peptide" is provided to C-terminus side of the light-chain variable region in the light-chain low-molecular-weight antibody.

The "carrier binding peptide" here only needs to be a peptide having a function to bind to a material of the carrier surface. The "carrier binding peptide" is not specifically limited in other specific amino acid sequence, length, or the like. Note that in the present invention, "binding" means interacting between the peptide and the carrier surface at a strength that is sufficient for use intended in the present invention. The term "binding" encompasses a case where the peptide has affinity for the carrier surface and adsorbs onto the carrier surface.

For example, preferably, the material of the carrier surface is plastic resin having been hydrophilized by property modification, the plastic resin being polystyrene, polycarbonate, polypropylene, polyethylene, polydimethylsiloxane (PDMS) or polymethyl methacrylate (PMMA). In a case where the above material is used as the material of the carrier surface, the carrier binding peptide is a peptide that has a function to bind to each of the plastic resin having been hydrophilized. For example, in a case where hydrophilic polystyrene is used as the material of the carrier surface, a peptide binding to hydrophilic polystyrene is selected.

For the carrier binding peptide, it is possible to use as appropriate any of conventionally known and reported peptides having a function to bind to each plastic resin having been hydrophilized. For example, as a peptide binding to hydrophilic polystyrene (hereinafter, also referred to as "PS-tag"), it is possible to use a peptide described in, for example, International Application Publication No. WO2009/101807 A1, other than a peptide used in Example described later. Specifically, the peptide may have a sequence RXXXR-RXRR (R: arginine, X: one or a combination of two or more of isoleucine (I), leucine (L), valine (V), alanine (A), glycine (G), methionine (M), serine (S) and threonine (T), shown in SEQ ID NO: 11 in the sequence listing of the present application) in this order from N terminus to C terminus. More specifically, it is possible to use a peptide having an amino acid sequence of any of SEQ ID NO: 1 to 20 disclosed in International Application Publication No. WO2009/101807A1. Note that Example described below employs PS-tag in which X is always isoleucine.

Further, as a peptide having a function to bind to hydrophilic polycarbonate (PC), it is possible to use, for example, a peptide disclosed in Publication of Japanese Translation of PCT International Application, Tokuhyo, No. 2004-518442 (Patent Application No. 2003-571248). Further, it is also possible to use a peptide uniquely found by the inventors of the present application. This peptide found by the inventors has an amino acid sequence of any of SEQ ID NO: 12 to 17 in the sequence listing of the present application and has a function to bind to PC. Note that the peptide of any of SEQ ID NO: 12 to 17 in the sequence listing of the present application has not been known at filing of the present application.

As a peptide having a function to bind to polymethyl methacrylate (PMMA) is, for example, a peptide described in (Literature of Serizawa et al. (Langmuir 2007, 23, 11127-11133)) or a peptide uniquely found by the inventors of the present invention. This peptide found by the inventors has an amino acid sequence of SEQ ID NO: 15, 18, or 19 in the sequence listing of the present application and has a function to bind to PMMA. Note that the peptide of SEQ ID NO: 15, 18, or 19 in the sequence listing of the present application has not been known at filing of the present application.

Among the above examples, it is particularly preferable to use, as described in Example below, (a) as the material of the carrier surface, polystyrene having been hydrophilized and (b) as the carrier binding peptide, a peptide binding to hydrophilic polystyrene. This combination allows formation of a strong bond between the peptide and the carrier even in the present of a surfactant or a denaturing agent.

The carrier binding peptide may directly bind to C terminus of the low-molecular-weight antibody or may bind to C terminus of the low-molecular-weight antibody via a suitable linker sequence. Further, to C terminus of the carrier binding peptide, a known tag sequence such as His tag may be provided.

In general, a surface of plastic resin that is preferable as the material of the carrier surface is hydrophobic. However, by carrying out various hydrophilization processes onto the surface of plastic resin, the plastic resin can be the carrier having a hydrophilic resin surface. For example, in the case of a polystyrene surface, a carrier having a hydrophilic polystyrene surface can be prepared by performing $UV+O_3$ treatment or plasma oxidation treatment. For a method of the hydrophilization treatment, it is possible to use a method described in International Application Publication No. WO2009/101807 A1.

As a carrier (substrate) material of the present invention, it is possible to use a conventionally known material such as various metal materials, a glass plate, and a ceramics plate other than resin. The carrier material is not specifically limited. The above-described plastic resin may be provided on a surface of the carrier material, and the carrier material with the plastic resin may be used as a substrate of the antibody-immobilized carrier of the present invention. The carrier may be in a form of a plate (including a wall surface or a bottom surface of a container or a well) or particles. As disclosed in Japanese Patent Application Publication, Tokukai, No. 2007-279018, if particulate plastic substrate whose surface has been subjected to hydrophilization is filled in a fluid handling section (each well) of a microwell plate, the low-molecular-weight antibody can be immobilized onto the particulate plastic substrate surface only by pouring solution containing the low-molecular-weight antibody into the well.

Further, the antibody-immobilized carrier of the present invention may also be used as a sensor chip for a surface plasmon resonance method (SPR method). In this case, for example, a thin film of plastic resin such as hydrophilic polystyrene is formed on a gold substrate and antibodies are immobilized onto the thin film.

As described above, in a plurality of antibody immobilized regions on the antibody-immobilized carrier of the present invention, different combinations of the heavy-chain low-molecular-weight antibody and the light-chain low-molecular-weight antibody each derived from a different antibody are immobilized. That is, antibody immobilized regions of the antibody-immobilized carrier of the present invention are configured such that antibodies each having different sets of a heavy chain and a light chain are immobilized in the antibody immobilized regions and the number of the different sets corresponds to the number of the different combinations. The larger the number of the antibody immobilized regions is, the more efficient screening of antibodies becomes. Therefore, the larger number of the antibody immobilized regions is preferable. Preferably, the number of the antibody immobilized regions are, for example, $10^2$, $10^4$, $10^6$, or $10^7$. More specifically, the number of combinations of a heavy chain and a light chain of antibodies within a living human body is considered to be $10^7$. In a case where $10^3$ heavy-chain low-molecular-weight antibodies and $10^3$ light-chain low-molecular-weight antibodies are prepared, the number of the combinations becomes $10^6$. In a case where $10^4$ heavy-chain low-molecular-weight antibodies and $10^3$ light-chain low-molecular-weight antibodies are prepared, the number of the combinations becomes $10^7$. Therefore, when the above preferable number of the antibody immobilized regions are provided, the number of the antibody immobilized regions can be substantially equal to the number of antibodies within a living human body. As a result, on one antibody-immobilized carrier, an antibody producing system within a living human body can be reproduced (In Vitro Domain Shuffling Technique).

As described in Example below, the inventors of the present invention demonstrated that it is possible to create a library of antibody fragments on a substrate by: (a) recovering antigenic specificity by successively immobilizing and assembling, onto a plastic carrier, Fab H and Fab L fragments to each of which a hydrophilic polystyrene binding peptide is fused; and (b) thoroughly covering all variations of a combination of Fab H and Fab L. In the "In Vitro Domain Shuffling technique" developed by the inventors of the present invention, various heavy-chain low-molecular-weight antibodies and light-chain low-molecular-weight antibodies are immobilized onto the carrier and this makes it possible to evaluate antigen binding activities. In other words, because an antibody library can be prepared, it becomes possible to identify an antibody (a combination of a heavy chain and a light chain) specific to an antigenic protein by carrying out immunoassay by using thus obtained antibody-immobilized carrier. Therefore, the antibody-immobilized carrier of the present invention is very useful in screening of antibody drug candidates and screening of antibodies for diagnosis.

In particular, in a case where a plurality of antibody immobilized regions are provided on an antibody-immobilized carrier, it is preferable to manage, by using a known arithmetic and logic unit such as a PC, positional information (coordinate information) of the heavy-chain low-molecular-weight antibody and the light-chain low-molecular-weight antibody on the carrier. In this configuration, for example, in a case where an causal substance (antigen, target molecule) of a specific disease is put in contact with the antibody-immobilized carrier, it is possible to specify a heavy chain and a light chain each having high antigenic specificity from coordinates from which a signal is obtained. Further, by putting a link to gene information of the heavy chain and the light chain that are immobilized, it is possible to obtain an antibody gene having high antigenic specificity.

As described above, according to the present invention, for example, it is possible to significantly reduce time, cost, and work for developing antigen drugs and to thoroughly obtain useful antibodies and antibody genes. Further, it also becomes possible to develop an antibody medicine (tailor made antibody medicine) corresponding to each individual patient in consideration of individual difference.

<2. Method of Producing Antibody-Immobilized Carrier>

A method, according to the present invention, of producing an antibody-immobilized carrier only need to include the step of: immobilizing a heavy-chain low-molecular-weight antibody including a heavy-chain variable region and a light-chain low-molecular-weight antibody including a light-chain variable region separately onto a carrier, so that an antibody immobilized region is prepared, the heavy-chain low-molecular-weight antibody and the light-chain low-molecular-weight antibody each being derived from an antibody recognizing a different antigen. In regard to other steps, conditions, materials, or the like, the method may employ conventionally known steps, conditions, materials, or the like, and are not specifically limited. More preferably, the step of immobilizing is repeated at least two times so that two or more of the antibody immobilized region are provided in an independent manner. This method of producing an antibody-immobilized carrier can be rephrased as a method of producing the antibody-immobilized carrier described in the section <1> above. Therefore, the explanation of the section <1> above can be referred to as appropriate for a part overlapping with the explanation of the section <1> above. Therefore, explanation of the part overlapping is omitted here and explanation in this section is specialized in a production method.

For example, in a case where the heavy-chain low-molecular-weight antibody and the light-chain low-molecular-weight antibody are prepared by a genetic recombination technique, the heavy-chain low-molecular-weight antibody and the light-chain low-molecular-weight antibody are generally obtained as insoluble aggregates as described above. In a case where such aggregates are used, the following method (so called a liquid phase refolding method) can be employed. In the method, first, the aggregates are subjected to solubilization by using a denaturing agent for collecting the aggregates. Then, the denaturing agent is removed by multi-stage dialysis, and then, refolding, purification, and quantitative measurement are carried out. Subsequently, by carrying out the step of immobilizing as described above, the heavy-chain low-molecular-weight antibody and the light-chain low-molecular-weight antibody are immobilized onto the carrier. Alternatively, it is also possible to employ the following method (so called a solid phase refolding method). In this method, for collecting the insoluble aggregates, the insoluble aggregates are solubilized by using a denaturing agent and put in contact with the carrier. Then, the denaturing agent is removed and refolding is carried out. Either of the liquid-phase refolding method and the solid phase refolding method can be used in the present invention. However, in view of a yield and efficiency (process and cost), the solid phase refolding method is preferable.

In other words, the step of immobilizing preferably includes: (a) the first sub-step of immobilizing, onto the carrier, insoluble aggregates of the heavy-chain low-molecular-weight antibody and the light-chain low-molecular-weight antibody by putting the denatured aggregates in contact with a carrier surface, the denatured insoluble aggregates each having been denatured by a denaturing agent and being in a denatured state; and (b) the second sub-step of refolding the heavy-chain low-molecular-weight antibody and the light-chain low-molecular-weight antibody each in the denatured state, by removing the denaturing agent from the heavy-chain low-molecular-weight antibody and the light-chain low-molecular-weight antibody that are in the denatured state and immobilized.

A concentration of the low-molecular-weight antibody contained in solution used in the first sub-step (a) is not specifically limited but can be set as appropriate. However, the concentration is preferably in a range of 0.1 µg/ml to 500 µg/ml, more preferably in a range of 0.5 µg/ml to 200 µg/ml, and most preferably in a range of 1 µg/ml to 100 µg/ml.

Here, the "denaturing agent" may be a general protein denaturing agent, surfactant, or the like, and is not specifically limited. Examples of the "denaturing agent" are protein denaturing agents such as urea and guanidine hydrochloride, and surfactants such as SDS and CHAPS. A concentration of the denaturing agent can be set as appropriate depending on an amount or type of the low-molecular-weight antibody employed here, and is not specifically limited. For example, as shown in Example explained later, in a case where the low-molecular-weight antibody is in a range of 5 µg/ml to 100 µg/ml, 0.5 M to 8 M urea is preferably used as the denaturing agent. More preferably, 0.5 M to 4 M urea is used, and most preferably, 0.5 M to 2 M urea is used. Note that here, a surfactant such as Tween20 may be used as an aggregation inhibitor. at the same time. In the method of immobilization, for example, (i) first, a high-concentration denaturing agent (e.g., 8 M) may be used to solubilize the insoluble aggregate; (ii) then the high-concentration denaturing agent may be diluted to a preferred concentration (in a range of 0.5 M to 2 M) of the denaturing agent, and (iii) subsequently, the insoluble aggregate is put in contact with the carrier for immobilization.

A time for denaturalization or a time for immobilization may be set as appropriate depending on an amount or type of the low-molecular-weight antibody, and is not specifically limited. In the step of immobilizing, a time for putting solution of the low-molecular-weight antibody in contact with the carrier is arranged to be, for example, in a range of 10 minutes to 10 hours, more preferably in a range of 30 minutes to 5 hours, and most preferably in a range of 1 hour to 3 hours.

A method for removing the denaturing agent in the second sub-step (b) may be a conventionally known method and is not specifically limited. For example, as described in Example below, the denaturing agent can be removed by general washup with a buffer. Note that in the above steps (a) and (b), a composition of a buffer used in solubilization of the low-molecular-weight antibody and a composition of washing for removing the denaturing agnet may be conventionally known compositions, respectively, and are not specifically limited. For example, compositions described in Example below can be suitably used.

Further, preferably, a set of the first sub-step and the second sub-step in the step of immobilizing is carried out, separately for each of the heavy-chain low-molecular-weight antibody and the light-chain low-molecular-weight antibody. That is, preferably, the heavy-chain low-molecular-weight antibody and the light-chain low-molecular-weight antibody are immobilized separately in multiple immobilization stages (e.g., two immobilization stages). For example, for the light-chain low-molecular-weight antibody, the first sub-step (a) is carried out so that the light-chain low-molecular-weight antibody denatured is immobilized onto the carrier, and then the second sub-step (b) is carried out so that the light-chain low-molecular-weight antibody denatured is refolded. Subsequently, preferably, for the heavy-chain low-molecular-weight antibody, the first sub-step (a) and the second sub-step (b) are similarly carried out. This is for the following reason. That is, as described in Example below, as compared to a case where the step of immobilizing is carried out by putting a mixture of the heavy-chain low-molecular-weight antibody and the light-chain low-molecular-weight antibody in contact with the carrier, remarkably superior antigen binding activity can be obtained in a case where the heavy-chain low-molecular-weight antibody and the light-chain low-molecular-weight antibody are separately immobilized.

In this way, in a case where the heavy-chain low-molecular-weight antibody and the light-chain low-molecularweight antibody are immobilized separately in multiple immobilization stages, the order as to which low-molecular-weight antibody is first immobilized onto the carrier is not specifically limited. However, preferably, the light-chain low-molecular-weight antibody is first immobilized by carrying out the first sub-step and the second sub-step, and then the heavy-chain low-molecular-weight antibody is immobilized by carrying out the first sub-step and the second sub-step. This is because, as described in Example below, immobilization in this order makes it possible to further enhance antigen binding ability of antibodies on the carrier.

According to the method of producing an antibody-immobilized carrier as described above, it is possible to efficiently produce a carrier onto which many combinations of a heavy chain and a light chain are immobilized. Each of the heavy chain and the light chain here is derived from a different antibody and has a lower molecular weight. Note, to make sure, that the present invention encompasses an antibody-immobilized carrier obtained by the production method described above.

<3. Antibody Screening Method>

An antibody screening method of the present invention only needs to include the step of: screening a heavy-chain low-molecular-weight antibody and/or a light-chain low-molecular-weight antibody each recognizing a specific antigen, by using the antibody-immobilized carrier as described above. Other steps, conditions, materials or the like of the method may be conventionally known steps, conditions, materials or the like, and are not specifically limited. It is possible to obtain a whole antibody by recloning the heavy-chain low-molecular-weight antibody and/or the light-chain low-molecular-weight antibody each selected by the antibody screening method of the present invention.

In a case where the "specific antigen" here is, for example, a target substance of an antibody medicine or a target substance of an antibody for diagnosis, it is possible to obtain the antibody medicine or the antibody for diagnosis. For example, in a case where a candidate antibody for an antibody medicine is to be selected, a target substance (antigen) of the antibody medicine is put in contact with the antibody-immobilized carrier as described above and an antibody recognizing specifically the antigen should be selected. Note that a method for evaluating antigen binding activity may be a conventionally known method and is not specifically limited. As described in Example described below, evaluation of the antigen binding activity can be carried out by, for example, ELISA employing a biotinylated antigen.

Further, the "specific antigen" used in the antibody screening method is preferably labeled for convenience of detection. As a labeling substance used as a marker is not specifically limited and may be, for example, a fluorescent dye, enzyme, protein, radioisotope, a chemiluminescent substance, biotin, and a color label substance.

A suitable substance of the fluorescent dye may be a substance that is used for labeling a substance such as a polypeptide or polynucleotide being generally an antigen and that is used for detection or quantitative determination. The fluorescent dye is not specifically limited. Examples of the fluorescent dye are fluorescein isothiocyanate (FITC), EHX (4,7,2', 4',5',7'-hexachloro-6-carboxylfluorescein, green fluorescent dye), fluorescein, NED (product name, manufactured by Applied Biosystems, yellow fluorescent dye) or 6-FAM (product name, manufactured by Applied Biosystems, yellowish green fluorescent dye), rhodamin or a derivative thereof (e.g., tetramethylrhodamin (TMR)), Alexa Fluor (Invitrogen), Cy Dye (GE Healthcare), and Quantum Dot (Invitrogen).

Further, the color label substance may be colloidal metal and colored latex. Typical examples of the colloidal metal are platinum colloid and gold colloid. A size of particles of the colloidal metal is generally in a range of approximately 3 nm to 100 nm in diameter. A typical example of the colored latex are synthesized latex such as polystyrene latex that is colored by pigment of each color such as red or green. The colored latex may be natural latex such as natural rubber latex. A size of the colored latex can be selected from a range of tens of nanometers to hundreds of nanometers in diameter. As these color label substances, commercial products may be directly used. Alternatively, in some cases, the color label substances may be further processed commercial products. As a further alternative, the color label substances themselves may be produced by a conventionally known method.

The heavy-chain low-molecular-weight antibody and/or the light-chain low-molecular-weight antibody selected by the antibody screening method of the present invention or a whole antibody obtained by cloning such a low-molecular-weight antibody can be used for various immunoassays including antigen-antibody reaction, for example, for application to in-vivo treatment and prevention, for application to in-vitro and in-vivo diagnosis, and for application to in-vitro assay and reagent. Note that in a case of the use in application to in-vivo treatment and prevention for human beings and application to diagnosis for human beings, it is preferable that the heavy-chain low-molecular-weight antibody and/or the light-chain low-molecular-weight antibody or the whole antibody is substantially a pure whole human antibody or a humanized antibody at least 90 to 95% or more, and more preferably 98 to 99% or more of which is an antibody portion derived from a human. A conventionally known method may be used as a technique for (i) analyzing an amino acid sequence of an antibody selected by the antibody screening method of the present invention and (ii) preparing the whole human antibody or the like.

The present invention encompasses a method of screening a human antibody (whole human antibody) recognizing a specific antigen by using the antibody-immobilized carrier as described above, the screening being carried out by using a chimeric antibody or a humanized antibody each recognizing the specific antigen.

In view of bioethics, it is impermissible to produce an antibody by immunizing humans with an antigen of interest. Therefore, all currently existing antibody drugs are developed in the form of chimeric antibodies each having a variable region of a mouse antibody and a constant region of a human antibody or humanized antibodies each obtained by transplanting, into a human antibody, only an antigen binding portion (CDR; complementary determining region) of a mouse antibody. However, there is a strong demand for development of a whole human antibody that has lower antigenicity and that is safer.

The above screening method of the present invention is developed in response to the above demand. The screening method allows obtaining, by using the In Vitro Domain Shuffling technique employing the antibody-immobilized carrier described above, a whole human antibody having antigenic specificity whose level is substantially equivalent to or higher than that of a chimeric antibody or humanized antibody. The screening method more specifically includes the following steps.

That is, in the first aspect, the method of screening a human antibody (whole human antibody) recognizing a specific antigen, the screening being carried out by using a chimeric antibody or a humanized antibody each recognizing the specific antigen, the heavy-chain low-molecular-weight antibody being immobilized onto the at least one antibody immobilized region and including a heavy-chain variable region derived from the chimeric antibody or the humanized antibody, the light-chain low-molecular-weight antibody being a light-chain low-molecular-weight antibody that is immobilized onto the at least one antibody immobilized region and that includes a light-chain variable region derived from a random human antibody, the method includes the steps of: (i) putting the specific antigen in contact with the antibody-immobilized carrier; (ii) detecting an antibody immobilized region recognizing the specific antigen on the antibody-immobilized carrier; and (iii) determining a light-chain low-molecular-weight antibody immobilized on the antibody immobilized region detected in the step (ii), as a candidate for a light-chain variable region of the human antibody recognizing the specific antigen.

Preferably, the method of screening further includes the steps of: (iv) putting the specific antigen in contact with another antibody-immobilized carrier including another antibody immobilized region onto which (a) the light-chain low-molecular-weight antibody determined as the candidate in the step (iii) and (b) a heavy-chain low-molecular-weight antibody including a heavy-chain variable region derived from a random human antibody are immobilized; (v) detecting an antibody immobilized region recognizing the specific antibody on the another antibody-immobilized carrier; and (vi) determining a heavy-chain low-molecular-weight antibody immobilized onto the antibody immobilized region detected in the step (v), as a candidate for a heavy-chain variable region of the human antibody recognizing the specific antigen.

The first aspect of the method of screening of the present invention may be described conceptually as follows. That is, the antibody-immobilized carrier in a preferred embodiment includes a plurality of antibody immobilized regions in each of which a heavy-chain low-molecular-weight antibody and a light-chain low-molecular-weight antibody are separately immobilized. Here, the heavy-chain low-molecular-weight antibody immobilized in the antibody immobilized region is a heavy-chain low-molecular-weight antibody that includes a heavy-chain variable region derived from a chimeric antibody or a human antibody. It has been previously confirmed that the chimeric antibody or the human antibody here has antigenic specificity against the specific antigen. Meanwhile, the light-chain low-molecular-weight antibody immobilized in a position for a light-chain low-molecular-weight antibody is a light-chain low-molecular-weight antibody including a light-chain variable region derived from a random human antibody. That is, the antibody-immobilized carrier prepared includes plural types of antibody immobilized regions each including a combination of (a) a known heavy-chain low-molecular-weight antibody including a heavy-chain variable region (preferably only one type) derived from a chimeric antibody or a human antibody and (b) a light-chain low-molecular-weight antibody including a light-chain variable region selected discretionarily from a library of light chains each derived from a human antibody. In regard to a variety of light chains of human antibodies, it is considered that there are approximately $10^3$ light chains. Accordingly, it is preferable to prepare approximately $10^3$ antibody immobilized regions. Ultimately, by putting an antigen in contact with the antibody-immobilized carrier configured as described above, antibody immobilized regions having high antigen binding activity are specified. Then, light-chain low-molecular-weight antibodies immobilized in thus specified antibody immobilized regions are selected. Thus selected light-chain low-molecular-weight antibodies are determined as candidates for light-chain variable regions of human antibodies each recognizing the specific antigen.

Subsequently, in antibody immobilized regions of another antibody-immobilized carrier additionally prepared, thus selected light-chain low-molecular-weight antibodies each including the light-chain variable region of a human antibody are immobilized. Further, as the heavy-chain low-molecular-weight antibodies, a plurality of heavy-chain low-molecular-weight antibodies each including a heavy-chain variable region derived from a random human antibody are immobilized. That is, the antibody-immobilized carrier additionally prepared includes plural types of antibody immobilized regions each including a combination of (a) a light-chain low-molecular-weight antibody including a light-chain variable region that is derived from a human antibody and that has been selected as a candidate and (b) a low-molecular-weight antibody including a heavy-chain variable region selected discretionarily from a library of heavy chains each derived from a human antibody. In regard to a variety of light chains of human antibodies, it is considered that there are approximately $10^4$ heavy chains. Accordingly, it is preferable to prepare approximately $10^4$ antibody immobilized regions. Ultimately, by putting an antigen in contact with the antibody-immobilized carrier configured as described above, antibody immobilized regions having high antigen binding activity are specified. Then, heavy-chain low-molecular-weight antibodies immobilized in thus specified antibody immobilized regions are selected. Thus selected heavy-chain low-molecular-weight antibodies are determined as candidates for the heavy-chain variable regions of human antibodies each recognizing the specific antigen. Note that though it is preferable to prepare approximately $10^4$ antibody immobilized regions, the number of the antibody immobilized regions may be arranged to be in a range of two or more to $10^2$ or in a range of $10^2$ to $10^3$ for reducing working hours and labors. Even in such a case, by using the invention of the present application, it is possible to obtain a whole human antibody capable of providing a sufficiently excellent effect.

By the above method, a combination of a light chain and a heavy chain each having high binding activity with respect to a specific antigen can be selected from a library of human antibodies. By using the combination of the light chain and the heavy chain selected as described above, a whole antibody having antigen binding activity whose level is equivalent to or higher than that of a chimeric antibody or a humanized antibody.

In the above aspect, first, a candidate for a light chain of a human antibody having high antigenic specificity is selected by using a combination of a light chain of a human antibody with a heavy chain of a chimeric antibody or a humanized antibody. However, the present invention is not limited to this aspect. For example, the present invention may be configured as follows: first, by using a combination of a heavy chain of a human antibody with a light chain of a chimeric antibody or a humanized antibody, a candidate for a heavy-chain low-molecular-weight antibody discretionarily selected from a heavy chain library of human antibodies is selected; and then, by using a combination of a light chain of a human antibody and thus selected candidate for the heavy chain, a candidate for a light chain of a human antibody having high antigenic specificity may be selected.

That is, in the second aspect, the method of the present invention of screening a human antibody recognizing a specific antigen by using the antibody-immobilized carrier as described above, the screening being carried out by using a chimeric antibody or a humanized antibody each recognizing the specific antigen, the light-chain low-molecular-weight antibody being immobilized onto the at least one antibody immobilized region and including a light-chain variable region derived from the chimeric antibody or the humanized antibody, the heavy-chain low-molecular-weight antibody being a heavy-chain low-molecular-weight antibody that is immobilized onto the at least one antibody immobilized region and that includes a heavy-chain variable region derived from a random human antibody, the method includes the steps of: (i) putting the specific antigen in contact with the antibody-immobilized carrier; (ii) detecting an antibody immobilized region recognizing the specific antigen on the antibody-immobilized carrier; and (iii) determining a heavy-chain low-molecular-weight antibody immobilized on the antibody immobilized region detected in the step (ii), as a candidate for a heavy chain variable region of the human antibody recognizing the specific antigen.

Preferably, the method of screening further includes the steps of: (iv) putting the specific antigen in contact with another antibody-immobilized carrier including another antibody immobilized region onto which (a) the heavy-chain low-molecular-weight antibody determined as a candidate in the step (iii) and (b) a light-chain low-molecular-weight antibody including a light-chain variable region derived from a random human antibody are immobilized; (v) detecting an antibody immobilized region recognizing the specific antibody on the another antibody-immobilized carrier; and (vi) determining a light-chain low-molecular-weight antibody immobilized onto the antibody immobilized region detected in the step (v), as a candidate for a light-chain variable region of the human antibody recognizing the specific antigen.

The above screening method is a two screening stage method arranged such that: first, a light chain (or a heavy chain) of a human antibody is once selected as a candidate; and then, a candidate for a heavy chain (or a light chain) derived from a human antibody having high antigen binding activity is selected by using a combination of a heavy chain (or a light chain) with the light chain (or a heavy chain) selected as the candidate. However, the present invention is not limited to this aspect. For example, the method may be configured to include the following steps (three screening stages) of: (a) selecting, as a candidate, a light chain (or a heavy chain) of a human antibody having high antigen binding activity by using a combination of the light chain (or the heavy chain) with a heavy chain (or a light chain) derived from a chimeric antibody or a humanized antibody; (b) selecting, as a candidate, a heavy chain (or a light chain) of a human antibody having high antigen binding activity by using a combination of the heavy chain (or the light chain) with a light chain (or a heavy chain) derived from a chimeric antibody or a humanized antibody; and (c) obtaining a whole human antibody having superior antigen binding activity by combining the candidates for the light chain and the heavy chain of the human antibodies, which light chain and heavy chain of the human antibodies are selected in the steps (a) and (b) that are separately carried out. The above aspect is preferable in that antigen binding activity can be examined in regard to a plurality of combinations of each of thus selected candidate for the light chain of the human antibody and thus selected candidate of the heavy chain of the human antibody.

In addition, the present invention encompasses a method of producing a human antibody, the method including the step of producing the human antibody by combining the candidate for the light-chain variable region of the human antibody and the candidate for the heavy-chain variable region of the human antibody, the candidate for the light-chain variable region and the candidate for the heavy-chain variable region being determined by the method of screening as described above. In other words, the method of the present invention of producing a human antibody includes the method of screening as one step.

A conventionally known method can be employed as a method for producing a whole human antibody from a candidate for a light chain selected from a light chain library of human antibodies and a candidate for a heavy chain selected from a heavy chain library of human antibodies. The method is not specifically limited. For example, the whole human antibody can be produced by a cloning technique or a chemical synthesis method employed in obtaining the "low-molecular-weight antibody" described above. For an explanation of the method of producing the whole human antibody, an explanation of the cloning technique or chemical synthesis method is referred to. For example, by employing the cloning technique, it is possible to collect a peptide having the amino acid sequence of the low-molecular-weight antibody by (i) first, preparing DNA encoding the above antibody, (ii) obtaining recombinant DNA, by inserting thus prepared DNA into an autonomously replicating vector, (iii) introducing as appropriate thus obtained recombinant DNA into a host such as $E.\ coli$, an animal cell or the like and thereby obtaining a transformant, and (iv) culturing the transformant and collecting the peptide from thus cultured material. Other than the method described above, an acellular protein synthesis system or a conventional peptide chemical synthesis method may also be employed. Further, a method for purifying an antibody may be a conventionally known method and is not specifically limited.

The present invention is not limited to the description of configurations above, but may be altered by a skilled person within the scope within the description in the present specification. An embodiment based on a proper combination of technical means disclosed in different embodiments is encompassed in the technical scope of the present invention. All literatures described in the present specification are incorporated herein as references. The following provides descriptions of the present invention in more detail by providing Example. However, the present invention is not limited to only the following Example.

EXAMPLE

1. Materials (1) Solubilization Buffer for Solubilizing Inclusion Body (pH 7.5)

6 M guanidine hydrochloride, 10 mM 2-mercaptoethanol, 2×PBS (2) Binding Buffer For Purifying Fab (pH 7.5) . . . . Solution A 8 M urea, 20 mM imidazole, 2×PBS (3) Elution Buffer For Purifying Fab (pH 7.5) . . . . Solution B 8 M urea, 400 mM imidazole, 2×PBS (4) Hydrophilic Polystyrene Support For Solid Phase Refolding (PS Plate)

96-well microplate for tissue culture (AGC Technoglass #3861-096)

(5) Color Solution For ELISA

100 μl of ABTS (Invitrogen: #00-2001) was 100-fold diluted with 0.1 M citric acid buffer (pH 4.0) and 0.03% $H_2O$, and used.

(6) Fab Expression Vector: pET22 (Novagen)

(7) Expression Host: $E.\ coli$ Rosetta (DE3) (Novagen)

2. Literatures Relevant to Antibody Genes Employed (1) Anti-RNase Antibody
Katakura Y, Kobayashi E, Kurokawa Y, Omasa T, Fujiyama K, Suga K.
Cloning of cDNA and Characterization of Anti-RNase A Monoclonal Antibody 3A21
Journal of Fermentation and Bioengineering. 82, 312-314 (1996)
(2) Anti-CRP Antibody
Dong Hwan Choi, Katakura Y, Ninomiya K, Shioya S. Rational Screening of Antibodies and Design of Sandwich Enzyme Linked Immunosorbent Assay on the Basis of a Kinetic Model
Journal of Bioscience and Bioengineering. 105, 261-272 (2008)
(3) Anti-ED-B Antibody and Anti-IFNG Antibody
Alessandro Pini, Francesca Viti, Annalisa Santucci, Barbara Carnemollai, Luciano Zardii, Paolo Neri, and Dario Neri
Design and Use of a Phage Display Library
The Journal of Biological Chemistry. 273, 21769-21776 (1998)

3. Preparation Of Low-Molecular-Weight Antibody (Fab and PS-tag Fused Fab)

All of the above literatures are relevant to scFv genes. Accordingly, in the present example, Fab gene was prepared by (i) isolating genes corresponding to VH and VL regions from scFv gene by PCR and (ii) fusing thus isolated genes with genes of $CH_1$ region and $C_k$ region, respectively. The followings are amino acid sequences of Fab and PS-tag fused Fab employed in Example. Note that N terminus of each of the Fab and PS-tag fused Fab employed here is arranged to be Methionine (M) that is a start codon. Note further that in a case without PS-tag, histidine tag (H×6) is added to an end of a sequence derived from pET22 at C terminus. Meanwhile, in a case with PS-tag, PS-tag sequence is added between sequences derived from pET and histidine tag (H×6) is added to C terminus.

Fab-H derived from mouse anti-RNase antibody (Fab H) . . . SEQ ID NO: 1
Fab-H derived from PS-tag fused mouse anti-RNase antibody (Fab H-PS) . . . SEQ ID NO: 2
Fab-L derived from mouse anti-RNase antibody (Fab L) . . . SEQ ID NO: 3
Fab-L derived from PS-tag fused mouse anti-RNase (Fab L-PS) . . . SEQ ID NO: 4
Fab-H derived from PS-tag fused mouse anti-CRP antibody (Fab H-PS) . . . SEQ ID NO: 5
Fab-L derived from PS-tag fused mouse anti-CRP antibody (Fab L-PS) . . . SEQ ID NO: 6
Fab-H derived from PS-tag fused human anti-ED-B antibody (Fab H-PS) . . . SEQ ID NO: 7
Fab-L derived from PS-tag fused human anti-ED-B antibody (Fab L-PS) . . . SEQ ID NO: 8
Fab-H derived from PS-tag fused human anti-IFNG antibody (Fab H-PS) . . . SEQ ID NO: 9
Fab-L derived from PS-tag fused human anti-IFNG antibody (Fab L-PS) . . . SEQ ID NO: 10

The following describes a method for preparing a specific low-molecular-weight antibody (Fab and PS-tag fused Fab).

(A) Culture of *E. coli*
First, recombinant *E. coli* was inoculated onto 10 ml of 2×YT medium (containing Amp and Cm) and precultured at 37° C. overnight. Then, thus obtained precultured solution was added to 50 ml of Overnight Express medium (Novagen) (containing Amp and Cm) so that $OD_{600}$ became equal to 0.1. Then, 24-hour culture at 37° C. at 200 rpm was carried out. After this culture, cultured solution was transferred to a centrifugation tube and 20-minute centrifugation was carried out. Then, supernatant was removed. Note that antibiotic substances Amp and Cm were added so that a concentration of Amp became 50 μg/ml and a concentration of Cm became 34 μg/ml in the 2×YT medium.

(B) Collection Of Inclusion Body
First, to the *E. coli* cells in the form of a pellet, 2.5 ml of BugBuster (Novagen), 1 mg/ml of lysozym, and 2.0 μl of Benzonase Nuclease (Novagen) were added and thus obtained mixture was vortexed. Then, a resulting mixture was poured separately into Eppendorf tubes and subjected to centrifugation (at 4° C., at 20000×g, and for 20 minutes). Further, after a supernatant was removed and 800 μl of distilled water was added, a resulting mixture was vortexed and subjected again to centrifugation (at 4° C., at 20000×g, and for 20 minutes). Subsequently, after a supernatant was removed, an inclusion body was collected. Ultimately, 5 ml of solubilization buffer was added, so that the inclusion body was dissolved.

(C) Purification By Affinity Chromatography
The following procedure was used for purifying low-molecular-weight antibodies that had been solubilized and that was in a denatured state. First, solutions A and B were prepared. Then, a chromatography system (AKTA) was turned on and the solutions A and B were set in Lines A and B, respectively. Contents of Lines A and B were replaced with solutions A and B, respectively. Then, His Trap™ HP column (GE HealthCare) was attached. Further, the solution A was supplied into the His Trap™ HP column at a flow rate of 1 ml/min so that an inside of this column was equilibrated. Furthermore, the low-molecular-weight antibodies having been solubilized was supplied at a flow rate of 1 ml/min and adsorbed to the column. Then, the solution A was supplied to the column at a flow rate of 1 ml/min and the column was washed. Subsequently, the solution B was supplied into the column at a flow rate of 1 ml/min and the column was washed. Then, Fab and PS-tag fused Fab were collected. After the collection, the low-molecular-weight antibodies were subjected to overnight dialysis against 8 M urea-1×PBS.

4. Preparation of Biotinylated Antigen

First, antigens (1 mg/ml) was dialyzed against 1 L of 1×PBS. Then, 1 mg of biotinamidocaproate N-hydroxysuccinimide ester was measured and taken. To this biotinamidocaproate N-hydroxysuccinimide ester, 10 μl of N,N-dimethylformamide was added and the biotinamidocaproate N-hydroxysuccinimide ester was dissolved (solution C). The antigens having been dialyzed as described above were transferred into a sample bottle. To this bottle, 10 μl of the solution C was added and gently stirred at a room temperature for one hour. Subsequently, overnight dialysis against 1 L of 1×PBS was carried out.

5. Antibody-Immobilized Carrier Employing Low-Molecular-Weight Antibody Derived from Mouse Anti-RNase Antibody A low-molecular-weight antibody derived from a mouse anti-RNase antibody was immobilized onto a hydrophilic PS plate by a solid phase refolding method. More specifically, first, the low-molecular-weight antibody Fab H or Fab H-PS (or Fab L or Fab L-PS) was diluted so that: (a) a final concentration of the low-molecular-weight antibody Fab H or Fab H-PS (or Fab L or Fab L-PS) became 100 µg/ml; (b) a final concentration of urea became 4 M; and (c) a final concentration of Tween 20 became 1%. Then, thus obtained mixture was incubated at a room temperature for 10 minutes. Then, 100 µl of the mixture was put on the hydrophilic PS plate, and incubated at 25° C. for one hour. Then, the hydrophilic PS plate was washed five times with 0.1% PBST, and the low-molecular-weight antibody Fab H was refolded on the hydrophilic PS plate. This operation was repeatedly carried out for each of Fab L, Fab L-PS and Fab H-PS and each of Fab L, Fab L-PS and Fab H-PS was immobilized onto a hydrophilic PS plate.

Figure 2:
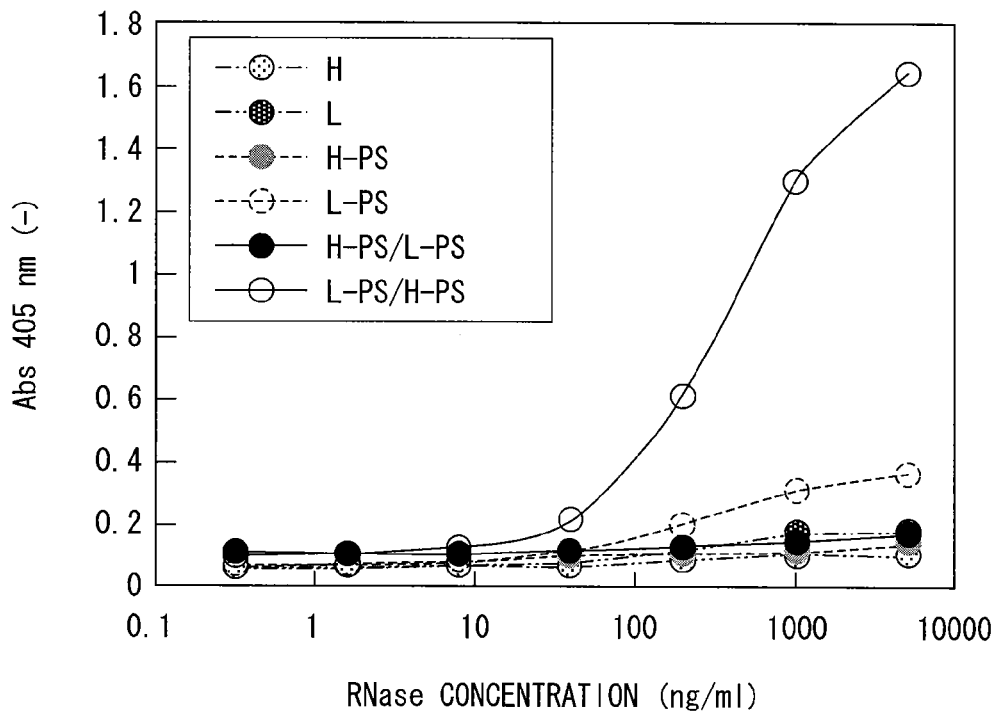

The following 6 ways of antibody-immobilized carriers were prepared:

Fab H-immobilized carrier (H)
Fab L-immobilized carrier (L)
Fab H-PS-immobilized carrier (H-PS)
Fab L-PS-immobilized carrier (L-PS)
Carrier (H-PS/L-PS) onto which Fab L-PS was immobilized after Fab H-PS had been immobilized onto the carrier
Carrier (L-PS/H-PS) onto which Fab H-PS was immobilized after Fab L-PS had been immobilized onto the carrier By using these antibody-immobilized carriers, each antigen binding activity of each low-molecular-weight antibody was examined by ELISA. More specifically, first, 300 µl of 2% BSA-PBST was added to the PS plate onto which the low-molecular-weight antibody was immobilized. Then, one-hour incubation at 25° C. was carried out, and the PS plate was washed with PBST five times. Further, 100 µl of biotinylated antigen (mouse RNase) diluted with 0.2% BSA-PBST to a concentration in a range of 0 µg/ml to 5 µg/ml, and one-hour incubation at 25° C. was carried out. Furthermore, the PS plate was washed with PBST five times. Next, 100 µl of HRP labeled streptavidin 5000-fold diluted with 0.2% BSA-PBST was added, and one-hour incubation at 25° C. was carried out. Subsequently, the PS plate was washed with PBST five times. Further, 100 µl of color solution was added, and 30-minute incubation at 25° C. was carried out. Then, absorbancy was measured. FIG. 2 show a result of this measurement. As shown in FIG. 2, antigen binding activity was obtained only in L-PS/H-PS.

6. Examination on Conditions for Solid Phase Refolding

Regarding conditions for solid phase refolding at immobilization of a low-molecular-weight antibody derived from mouse anti-RNase antibody onto a hydrophilic PS plate, examination was carried out. The following is a specific method of the examination. First, the low-molecular-weight antibody was immobilized onto the hydrophilic PS plate in the same manner as described in the section <5> above except that a final concentration of the low-molecular-weight antibody (Fab H, Fab H-PS, Fab L or Fab L-PS) was set at 5 µg/ml and a final concentration of urea was set at 4M, 2M, 1M, or 0.5M. For each of different combinations of low-molecular-weight antibodies, the operation was repeatedly carried out. As a result, the following 5 types of antibody-immobilized carriers were prepared.

Figure 3:
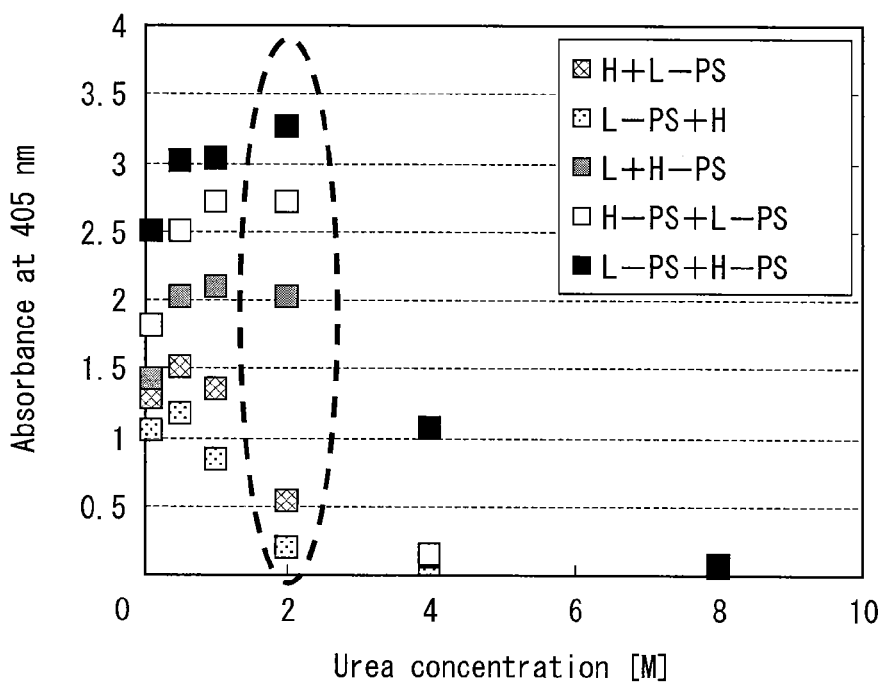

Carrier (H+L-PS) onto which Fab L-PS was immobilized after Fab H had been immobiliazed onto the carrier
Carrier (L-PS+H) onto which Fab H was immobilized after Fab L-PS had been immobilized onto the carrier
Carrier (L+H-PS) onto which Fab H-PS was immobilized after Fab L had been immobilized onto the carrier
Carrier (H-PS+L-PS) onto which Fab L-PS was immobilized after Fab H-PS had been immobilized onto the carrier
Carrier (L-PS+H-PS) onto which Fab H-PS was immobilized after Fab L-PS had been immobilized onto the carrier By using these antibody-immobilized carriers, antigen binding activity of each low-molecular-weight antibody was examined by ELISA. Here, ELISA was carried out in the same manner as described in the section <5> except that the concentration of the biotinylated antigen (mouse RNase) employed was set at 1 µg/ml. FIG. 3 shows a result of this examination.

As shown in FIG. 3, in a case where the concentration of urea was in a range of 0.5 M to 2 M, antigen binding activity was higher in the order of L-PS+H-PS, H-PS+L-PS, L+H-PS, H+L-PS, and L-PS+H. Note that in a case where the concentration of urea was 4 M, antigen binding activity was seen only in L-PS+H-PS.

7. Antibody-Immobilized Carriers Each Employing Low-Molecular-Weight Antibody Derived from Mouse Anti-CRP Antibody, Mouse Anti-RNase Antibody, Human Anti-IFNG Antibody Or Human Anti-ED-B Antibody Antibody-immobilized carriers were prepared by immobilizing one or a combination of Fab H-PS and Fab L-PS each derived from any of mouse anti-CRP antibody, mouse anti-RNase antibody, human anti-IFNG antibody and human anti-ED-B antibody. First, after one of the above types of Fab L-PS was immobilized onto a hydrophilic PS plate, one of the above types of Fab H-PS was immobilized. This immobilization was carried out in the same manner as described in the above sections <5> and <6> except that the final concentration of each of Fab L-PS and Fab H-PS was set at 5 µg/ml and the final concentration of urea was set at 2 M. The above operation was repeatedly carried out for each of different combinations of one of the above types of Fab L-PS and one of the above types of Fab H-PS. As a result, 16 types of the antibody-immobilized carriers covering all combinations of Fab L-PS and Fab H-PS of the above types were prepared. In addition, 8 types of antibody-immobilized carriers on each of which only one of Fab L-PS and Fab H-PS of the above types was immobilized.

Antigen binding activity of each of Fab L-PS and Fab H-PS above was examined by ELISA by using mouse RNase, mouse CRP, human ED-B and human IFNG as antigens. Here, ELISA was carried out in the same manner as described in the section <6>. FIGS. 4 to 7 show detection results. In FIGS. 4 to 7, "w/o H" means that Fab H-PS was not immobilized and only Fab L-PS was immobilized. Similarly, "w/o L" indicates that Fab L-PS was not immobilized and only Fab H-PS was immobilized. Moreover, in a case where a vertical axis of the graph is labeled "H ED-B", a bar of "L ED-B" shows a result of antigen binding activity of a PS plate onto which Fab L-PS and Fab H-PS each derived from human anti-ED-B antibody were immobilized.

Figure 4:
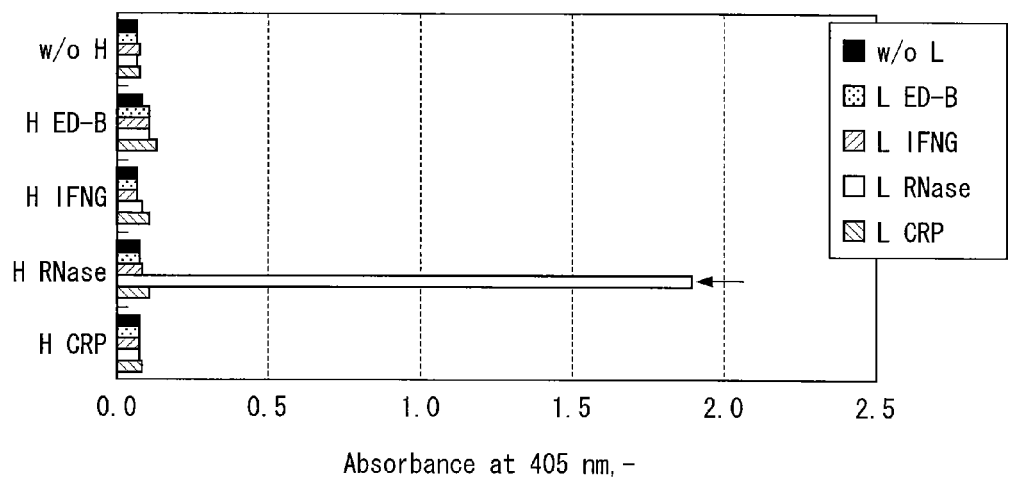
Figure 5:
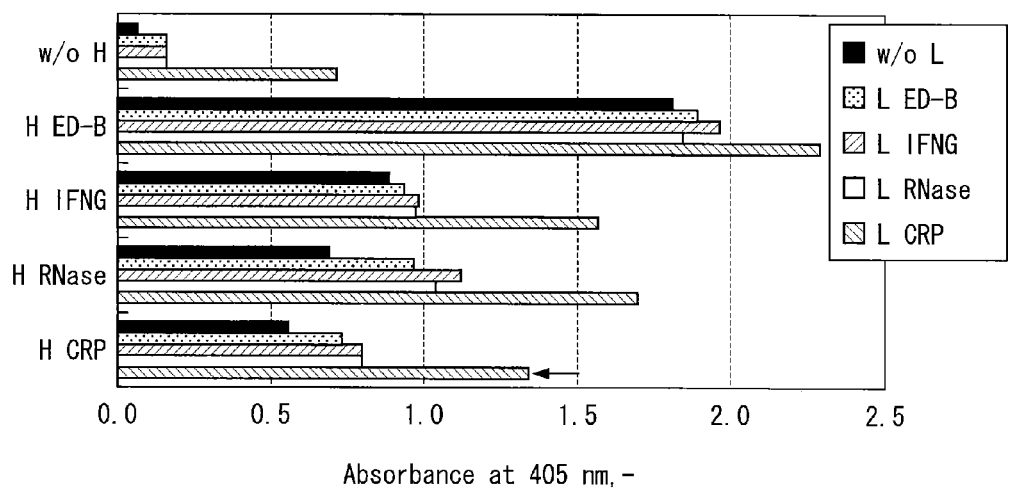
Figure 6:
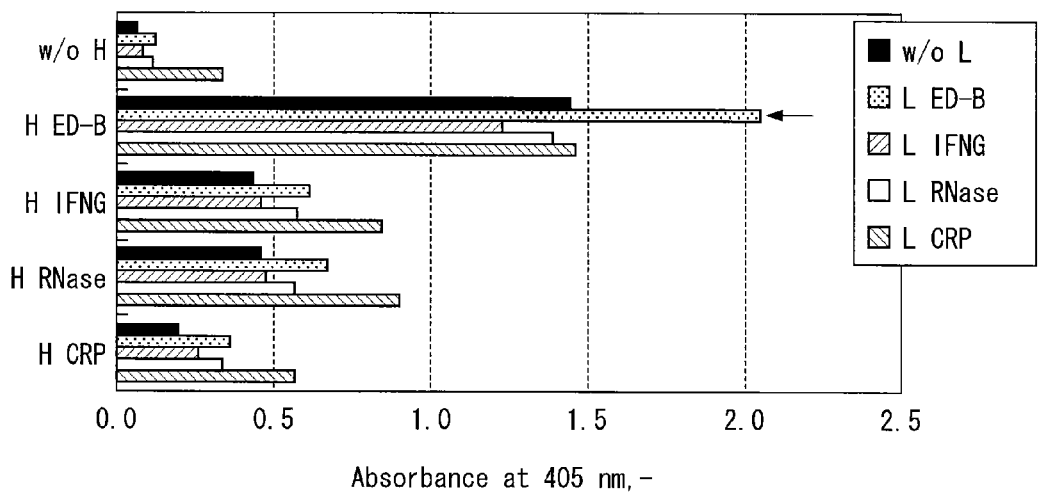
Figure 7:
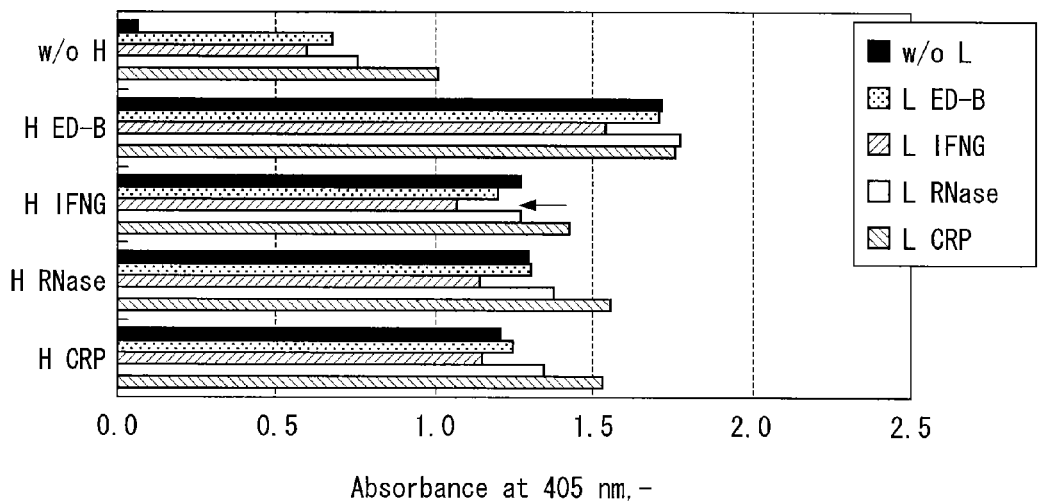

As shown in FIG. 4, in a case where mouse RNase was used as an antigen, only the PS plate onto which Fab L-PS and Fab H-PS each derived from mouse anti-RNase antibody were immobilized had antigen binding activity. As shown in FIG. 5, in a case where mouse CRP was used as an antigen, in regard to light chains, Fab L-PS derived from mouse anti-CRP antibody had high antigen binding activity. However, in this case, in regard to heavy chains, Fab H-PS derived from human anti-ED-B antibody had high antigen binding activity. A combination of Fab L-PS derived from mouse anti-CRP antibody and Fab H-PS derived from human anti-ED-B antibody had the highest antigen binding activity. FIG. 6 shows a case where human ED-B was used as an antigen. In this case, Fab L-PS derived from mouse anti-CRP antibody had high antigen binding activity in a case where the heavy chain was Fab H-PS that was derived from an antibody except human anti-ED-B antibody. Meanwhile, in regard to a combination of a heavy chain and a light cahin, a combination of Fab L-PS and Fab H-PS each derived from human anti-ED-B antibody had the highest antigen binding activity. FIG. 7 shows a case where human IFNG was used as an antigen, specificity was found in neither Fab H-PS nor Fab L-PS and, in this case, it was considered that binding to the antigen occurs depending on Fab H.

8. Examination of Antigen Binding Activity of Low-Molecular-Weight Antibody in Relation to Difference in Immobilization Method Examination was carried out on difference in antigen binding activity due to difference in immobilization method in preparing a carrier onto which one or a combination of Fab H, Fab L, Fab H-PS, and Fab L-PS each derived from mouse anti-RNase antibody was immobilized. Specifically, the following cases (i) to (iii) were compared: (i) a case where a heavy-chain low-molecular-weight antibody or a light-chain low-molecular-weight antibody was solely immobilized; (ii) a case where a heavy-chain low-molecular-weight antibody and a light-chain low-molecular-weight antibody in a mixed state were immobilized at the same time; and (iii) a case where a heavy-chain low-molecular-weight antibody and a light-chain low-molecular-weight antibody were successively immobilized in multiple stages. A specific method for the examination was as follows:

(i) Case where Low-Molecular-Weight Antibody Alone was Immobilized

Figure 8:
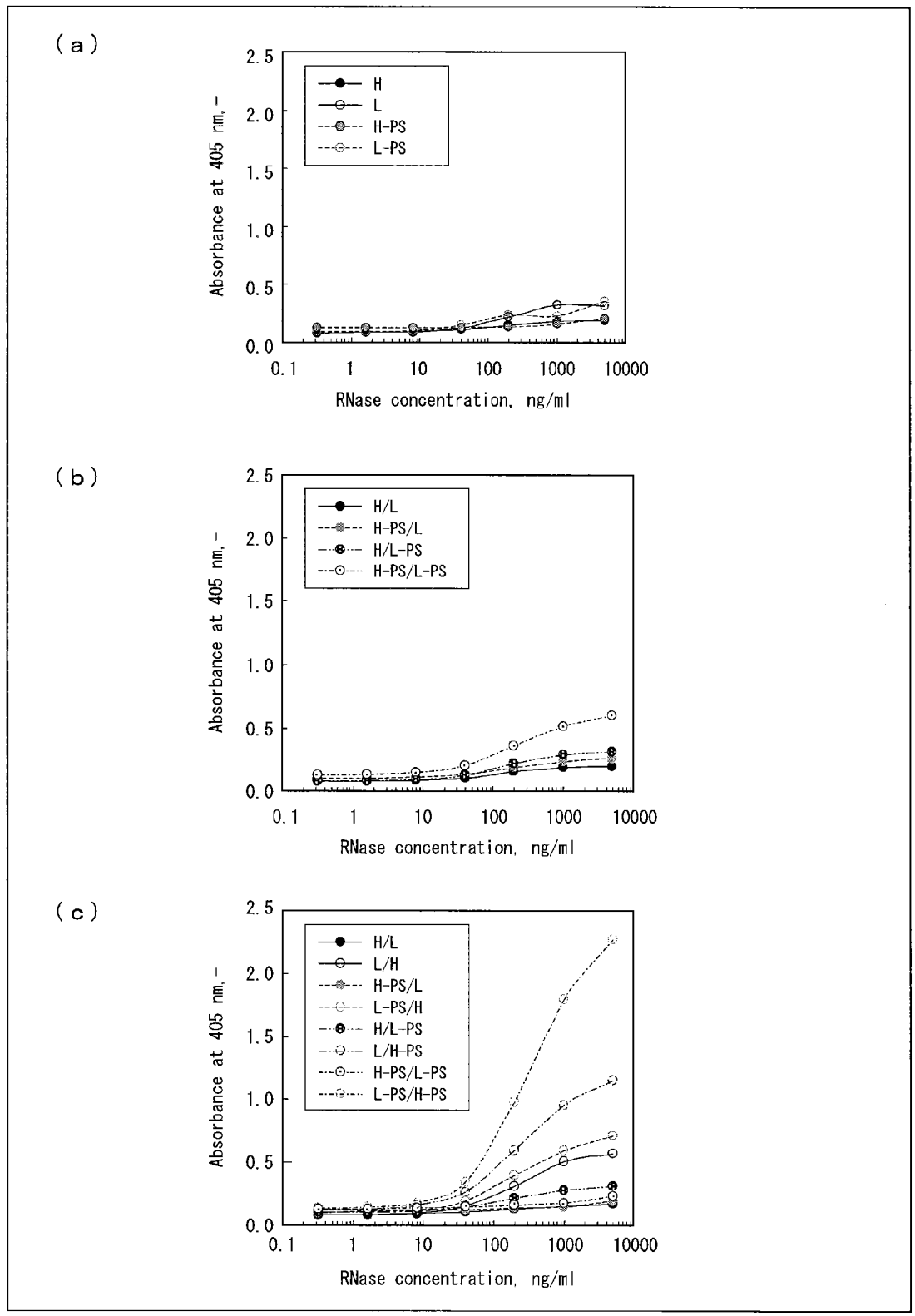

First, any one of Fab H, Fab H-PS, Fab L and Fab L-PS was diluted so that: (a) a final concentration of this low-molecular-weight antibody was 200 µg/ml; (b) a final concentration of urea was 4 M; and (c) a final concentration of Tween 20 was 1%. Then, 10-minute incubation at a room temperature was carried out. Further, 100 µl of thus obtained mixture was provided on a hydrophilic PS plate and one-hour incubation at 25° C. was carried out. Then, the hydrophilic PS plate was washed with PBST five times. Further, the any one of Fab H, Fab H-PS, Fab L and Fab L-PS was refolded on the hydrophilic PS plate. (a) of FIG. 8 shows a result of the examination on antigen binding activity.

(ii) Case where Low-Molecular-Weight Antibodies Mixed were Immobilized

First, a combination of (a) Fab H or Fab H-PS and (b) Fab L or Fab L-PS was diluted so that: (a) a final concentration of each of these low-molecular-weight antibodies was 200 µg/ml (a final concentration of a sum of the combination of these low-molecular-weight antibodies was 400 µg/ml); (b) a final concentration of urea was 4 M; and (c) a final concentration of Tween 20 was 1%. Then, 10-minutes incubation at a room temperature was carried out. Further, 100 µl of thus obtained mixture was provided on a hydrophilic PS plate and one-hour incubation at 25° C. was carried out. Then, the hydrophilic PS plate was washed with PBST five times. Further, the low-molecular-weight antibodies of the combination were refolded on the hydrophilic PS plate. (b) of FIG. 8 shows a result of the examination on antigen binding activity.

(iii) Case where Low-Molecular-Weight Antibodies were Successively Immobilized in Multiple Stages Except that the final concentration of each of the low-molecular-weight antibodies was arranged to be 200 µg/ml, the low-molecular-weight antibodies were immobilized in the same manner as described in the section <5> above. (c) of FIG. 8 shows a result of antigen binding activity.

As shown in (a) to (c) of FIG. 8, in both of (i) the case where a low-molecular-weight antibody alone was immobilized and (ii) the case where low-molecular-weight antibodies mixed were immobilized, antigen binding activity was hardly found. Only in (iii) the case where the low-molecular-weight antibodies were successively immobilized in multiple stages, antigen binding activity was found. Particularly in a case where Fab H or Fab H-PS was immobilized onto a carrier after Fab L or Fab L-PS had been immobilized onto the carrier, excellent antigen binding activity was found.

9. Experiment of Screening of Anti-AFP Antibody from Mouse Antibody Library

First, first-stage screening was carried out. The first-stage screening was screening of a heavy chain (H chain) and a light chain (L chain) each having affinity for an antigen. The following explains specific procedures.

(1) Amplification of Antibody Gene from Mouse Immunized with AFP;

As an antigen, α-fetoprotein (AFP) that is a diagnosis marker for liver cancer was used. Every week, a mouse was immunized with 50 µg of AFP, and the mouse was immunized four times in total. Then, in the fifth week, a spleen was taken out. Then, Total RNA in the spleen was collected and gene clusters of Fab H and Fab L of an antibody was amplified by RT-PCR. The gene clusters of Fab H and Fab L were subjected to ligation at Nde I/Not I site of PS-tag fused protein expression vector pET-PS19-6. Then, $E.\ coli$ BL21 (DE3) Rosetta was transformed by using the vector having been subjected to the ligation. Further, a single colony of thus transformed $E.\ coli$ was formed on an LB-ampicillin plate. Then, $E.\ coli$ into which a Fab H gene cluster was introduced was defined as a Fab H-PS $E.\ coli$ library ($1\times10^5$ colonies). Meanwhile, $E.\ coli$ into which a Fab L gene cluster was introduced was defined as a Fab L-PS $E.\ coli$ library ($1\times10^5$ colonies).

(2) High-Throughput Production of PS-Tag Fused Fab H (Fab H-PS) and PS-Tag Fused Fab L (Fab L-PS) by using Microplate;

First, into each well of a 96-well deep well plate (manufactured by Greiner Bio-One, 780271), 1 ml of Overnight Express TB medium (Merk) was provided. The Overnight Express TB medium contained 50 µg/ml of ampicillin and 34 µg/ml of chloramphenicol. The number of such a 96-well deep well plate prepared was 20. Then, a single colony was picked from the Fab H-PS $E.\ coli$ library obtained by forming single colonies on an LB-ampicillin plate. Further, thus picked single colony was inoculated in each well of the above-described deep well plate. In a similar manner, a single colony from the Fab L-PS $E.\ coli$ library was also inoculated. More specifically, for each of the Fab H-PS $E.\ coli$ library and the Fab L-PS $E.\ coli$ library, 10 plates (960 colonies) were used for inoculation. Then, the 96-well deep well plate was incubated at 37° C. at 1400 rpm for 24 hours.

(3) Bacterial Cell Disruption and Solubilization Of Inclusion Body;

Next, the 96-well deep well plate was subjected to centrifugation at 5000 rpm for 20 min, and supernatant was removed. Then, 200 µl of disrupted cell solution (20 ml of BugBuster, 20 mg of Lysozyme, and 6 µl of benzonaze) was added to each well, and the deep well plate was shaken at 37° C. at 1800 rpm for one hour. Furthermore, after centrifugation at 5000 rpm for 20 min, supernatant was removed. Then, 200 µl of ion exchanged water was added to each well and suspended. The above operation was repeated twice. Subsequently, after centrifugation at 5000 rpm for 20 min was carried out, 500 μl of a solubilizing solution (50 ml of 8 M Urea PBS, and 35 μl of mercaptoethanol) was added to each well. Then, the deep well plate was shaken at 25° C. at 14000 rpm for one hour. Subsequently, centrifugation at 5000 rpm for 20 min was carried out, and Fab H-PS and Fab L-PS contained in supernatant was purified as follows.

(4) Purification of Fab H-PS and Fab L-PS by Using Filter Plate;

To a 96-well filter plate (Whatman), 200 μl/well of 50% Ni Sepharose 4B (GE HealthCare) resin was added. Then, equilibration was performed by using 200 μl of Binding Buffer 1 (8 M urea-2×PBS, 20 μM imidazole). Into each well of the 96-well filter plate, 500 μl of a sample from the 96-well deep well plate was added. By pipetting, the above resin and the sample were gently mixed and then 20-minute incubation was carried out. Then, sample solution was sucked by an aspirator and removed. Next, the filter plate was washed once with 400 μl of Binding Buffer 1, and further washed twice with 200 μl of Binding Buffer 1. In addition, the filter plate was washed with Binding Buffer 2 (8 M urea-1×PBS, and 20 μM of imidazole), and subsequently, solution was removed by an aspirator.

Then, (i) to each well of the filter plate, 250 μl of Elution Buffer (8 M urea-400 mM of imidazole-1×PBS) was added and incubation was carried out for 20 minutes so that Fab H-PS and Fab L-PS each adsorbed to resin was eluted. Further, (ii) the 96-well filter plate was overlapped with a 800-μl 96-well deep well plate (Greiner Bio-One) and thus eluted solution was collected by centrifugation (500 g, for 5 min) into the 800-μl 96-well deep well plate for collection. This operation was repeated twice. Subsequently, the operations (i) and (ii) above were repeated once again.

(5) Isolation of Clone with High Affinity for AFP from Fab H-PS Library and Fab L-PS Library As a 96-well PS plate for screening, a Black plate (BD Falcon #353241) for fluorescence measurement was used. First, this PS plate was irradiated with oxygen plasma at 30 W for one minute, so that a surface of the PS plate became hydrophilic. After 75 μl of 1.33% Tween PBS was added to each well, 25 μl of a Fab H-PS library or a mouse H chain library was added to each well. Then, the Fab H-PS library or the mouse H chain library was incubated at 4° C. overnight. Then, after the PS plate was washed with 0.1% Tween PBS, 270 μl of 2% BSA-0.1% Tween PBS was added to each well. Next, the PS plate was subjected to blocking for one hour. Further, after the PS plate was washed with 0.1% Tween PBS, 1 μg/ml Alexa Fluor647-labeled AFP was prepared by using 0.2% BSA-0.1% Tween PBS. After 100 μl of thus obtained Alexa Fluor647-labeled AFP was added to each well, one-hour incubation was carried out while light was shielded. Subsequently, after the PS plate was washed with 0.1% Tween PBS, fluorescence intensity was measured by using a fluorescence plate reader (TECAN infinite M200) (excitation wavelength: 645 nm, fluorescence wavelength: 678 nm).

Figure 9:
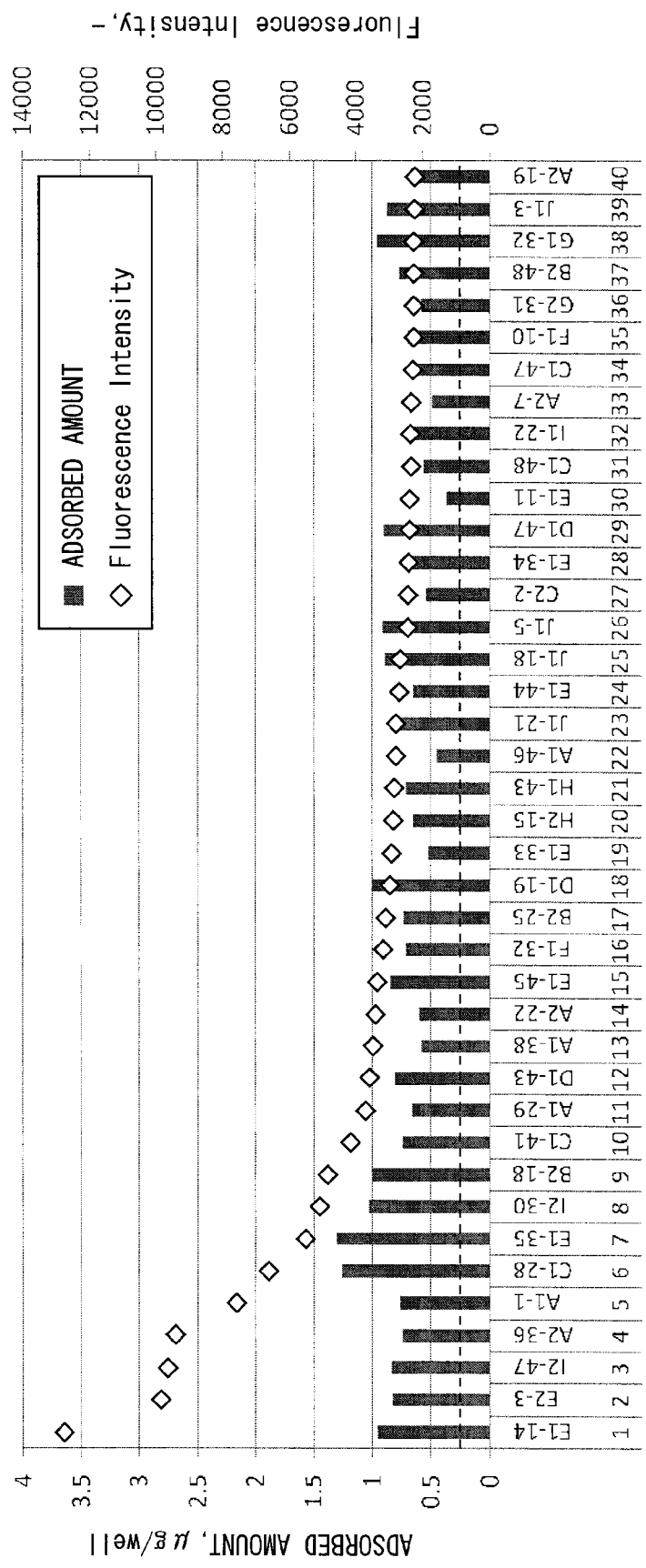
FIG. 9 is a diagram showing a result of examination on top 40 clones which have higher affinity for AFP and which are selected from among a mouse Fab H-PS library (960 types), in regard to affinity for an antigen (light emission intensity).
Figure 10:
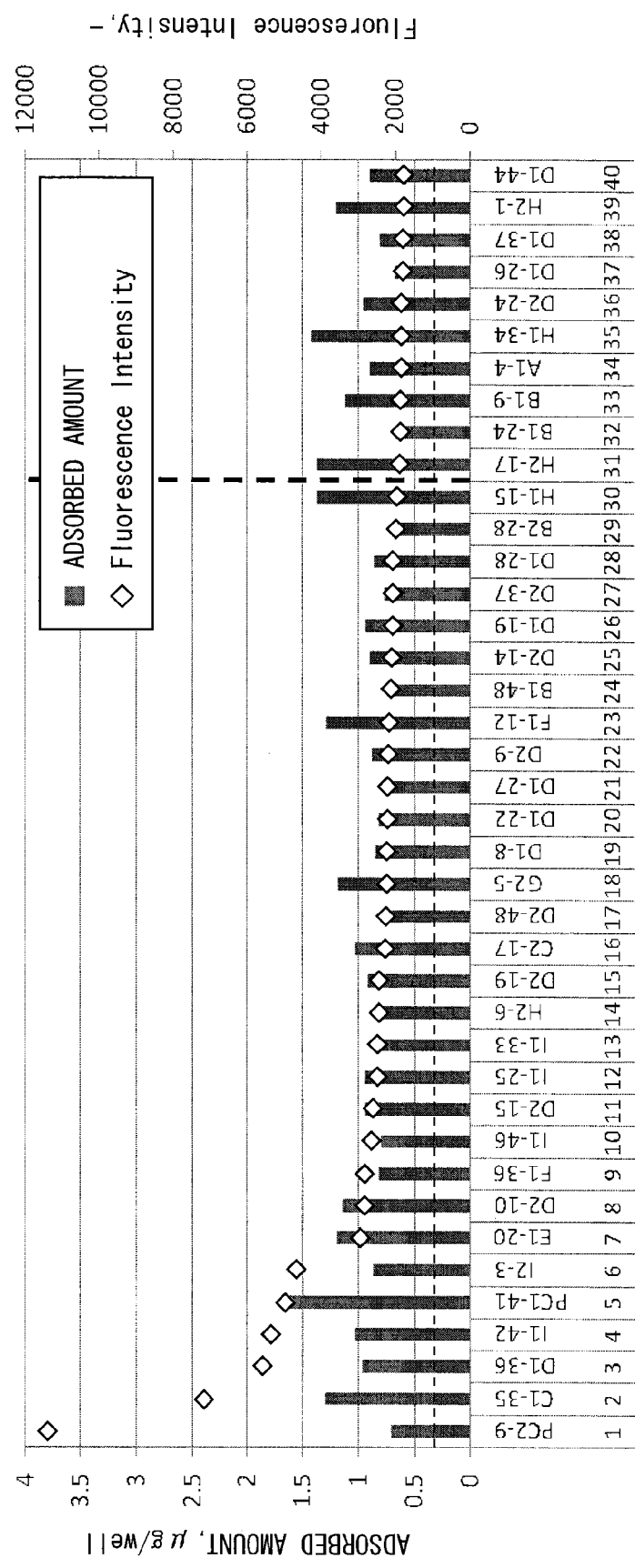
FIG. 10 is a diagram showing a result of examination on top 30 clones which have higher affinity for AFP and which are selected from a mouse Fab L-PS library (960 types), in regard to affinity for an antigen.

Top 40 types of Fab H-PS clones and top 30 types of Fab L-PS clones in the order of higher fluorescence intensity were selected and used in the following steps. FIGS. 9 and 10 show results of the following steps. Note that bar graphs of FIGS. 9 and 10 show adsorbed amount (scale on the left side) and dots shows fluorescence intensity (scale on the right side). Note that an average signal intensity of 960 clones of H chain was 1086. Meanwhile, an average signal intensity (fluorescence intensity) of 960 clones of L chain was 1028.

(6) Production of Fab Library Plate by Using In Vitro Domain Shuffling and Screening of Fab with High Affinity for AFP;

By using the 40 types of Fab H-PS clones and the 30 types of Fab L-PS clones selected above, 1200 types (H chain: 40 types×L chain: 30 types) of antibody libraries were prepared on a substrate. Then, antigen binding ability was evaluated (second-stage screening). The following explains specific procedure for the evaluation.

As a 384-well PS plate for screening, a Black plate (BD Falcon #353285) for fluorescence measurement was used. First, this PS plate was irradiated with oxygen plasma at 30 W for one minute, so that a surface of the PS plate became hydrophilic. After 30 μl of 1.33% Tween PBS was added to each well, 10 μl of each of the top 30 types of Fab L-PS clones from the Fab L-PS library was added to each well. Then, the 384-well PS plate was incubated at 25° C. for 2 hours. Further, after 30 μl of 1.33% Tween PBS was added to each well, 10 μl of each of the top 40 types of clones from the Fab H-PS library was added to each well. Then, 2-hour incubation at 25° C. was carried out. Next, after the PS plate was washed with 0.1% Tween PBS, 80 μl of 2% BSA-0.1% Tween PBS was added to each well. Next, this PS plate was subjected to blocking for one hour. Further, after the PS plate was washed with 0.1% Tween PBS, 1 μg/ml Alexa Fluor647-labeled AFP was prepared by using 0.2% BSA-0.1% Tween PBS. After 100 μl of thus obtained Alexa Fluor647-labeled AFP was added to each well, one-hour incubation was carried out while light was shielded. Subsequently, after the PS plate was washed with 0.1% Tween PBS, fluorescence intensity was measured by using a fluorescence plate reader (TECAN infinite M200) (excitation wavelength: 645 nm, fluorescence wavelength: 678 nm).

Consequently, a heavy-chain and light-chain combination whose signal of fluorescence intensity was 5000 or higher was determined as an anti-AFP antibody. As a result, the following 9 combinations were determined as anti-AFP specific antibodies for liver cancer: (H3, L4), (H3, L6), (H3, L12), (H6, L6), (H8, L6), (H8, L15), (H19, L9), (H20, L9) and (H35, L6). Note that H in parentheses means a heavy chain and numerals in parentheses show the order of H chains shown in FIG. 9. Similarly, L in parentheses means a light chain and numerals in parentheses show the order of L chain shown in FIG. 10. In other words, each of these heavy-chain and light-chain combinations was found to be useful as an anti-AFP antibody.

10. Conversion of Chimeric Antibody into Human Antibody by Using Human Antibody Library By using In Vitro Domain Shuffling, the following experiment was carried out for obtaining a whole human antibody having antigenic specificity whose level is equivalent to or higher than that of a chimeric antibody.

(1) Amplification of Human Antibody Gene;

From human spleen Total RNA (Clontech, #636525), gene clusters of Fab H and Fab L of a human antibody was amplified by RT-PCR. The gene clusters of Fab H and Fab L were subjected to ligation at Nde I/Not I site of PS-tag fused protein expression vector pET-PS 19-6. Then, E. coli BL21 (DE3) Rosetta was transformed by using the vector having been subjected to the ligation. Further, a single colony of thus transformed E. coli was formed on an LB-ampicillin plate. Then, E. coli into which a Fab H gene cluster was introduced was defined as a Fab H-PS E. coli library ($1\times10^6$ colonies).

Meanwhile, *E. coli* into which a Fab L gene cluster was introduced was defined as a Fab L-PS *E. coli* library (1×10$^6$ colonies).

(2) High-Throughput Production of PS-Tag Fused Fab H (Fab H-PS) and PS-Tag Fused Fab L (Fab L-PS) by Using Microplate;

First, into each well of a 96-well deep well plate (manufactured by Greiner Bio-One, 780271), 1 ml of Overnight Express TB medium (Merk) was provided. The Overnight Express TB medium contained 50 μg/ml of ampicillin and 34 μg/ml of chloramphenicol. The number of such a 96-well deep well plate prepared was 20. Then, a single colony was picked from the Fab H-PS *E. coli* library obtained by forming single colonies on an LB-ampicillin plate. Further, thus picked single colony was inoculated in each well of the above-described deep well plate. In a similar manner, a single colony from the Fab L-PS *E. coli* library was also inoculated. (10 plates (960 colonies) for each of the Fab H-PS *E. coli* library and the Fab L-PS *E. coli* library). Then, the 96-well deep well plate was incubated at 37° C. at 1400 rpm for 24 hours.

(3) Bacterial Cell Disruption and Solubilization of Inclusion Body;

Next, the 96-well deep well plate was subjected to centrifugation at 5000 rpm for 20 min, and supernatant was removed. Then, 200 μl of disrupted cell solution (20 ml of Bugbuster, 20 mg of Lysozyme, and 6 μl of benzonaze) was added to each well, and the deep well plate was shaken at 37° C. at 1800 rpm for one hour. Furthermore, after centrifugation at 5000 rpm for 20 min, supernatant was removed. Then, 200 μl of ion exchanged water was added to each well and suspended. The above operation was repeated twice. Subsequently, after centrifugation at 5000 rpm for 20 min was carried out, 500 μl of a solubilizing solution (50 ml of 8 M Urea PBS, and 35 μl of mercaptoethanol) was added to each well. Then, the deep well plate was shaken at 25° C. at 14000 rpm for one hour. Subsequently, centrifugation at 5000 rpm for 20 min was carried out, and Fab H-PS and Fab L-PS contained in supernatant was purified as follows.

(4) Purification of Fab H-PS and Fab L-PS by Using Filter Plate;

To a 96-well filter plate (Whatman), 200 μl/well of 50% Ni Sepharose 4B (GE HealthCare) resin was added. Then, equilibration was performed by using 200 μl of Binding Buffer 1 (8 M urea-2×PBS, 20 μM imidazole). Into each well of the 96-well filter plate, 500 μl of a sample from the 96-well deep well plate was added. By pipetting, the above resin and the sample were gently mixed and then 20-minute incubation was carried out. Then, sample solution was sucked by an aspirator and removed. Next, the filter plate was washed once with 400 μl of Binding Buffer 1, and further washed twice with 200 μl of Binding Buffer 1. In addition, the filter plate was washed with Binding Buffer 2 (8 M urea-1×PBS, and 20 μM of imidazole), and subsequently, solution was removed by an aspirator.

Then, (i) to each well of the filter plate, 250 μl of Elution Buffer (8 M urea-400 mM of imidazole-1×PBS) was added and incubation was carried out for 20 minutes so that Fab H-PS and Fab L-PS each adsorbed to resin was eluted. Further, (ii) the 96-well filter plate was overlapped with a 800-μl 96-well deep well plate (Greiner Bio-One) and thus eluted solution was collected by centrifugation (500 g, for 5 min) into the 800-μl 96-well deep well plate for collection. This operation was repeated twice. Subsequently, the operations (i) and (ii) above were repeated once again.

(5) Evaluation of Rituxan (Registered Trademark) Chimeric Fab H-PS/Human Fab L-PS Library by Using In Vitro Domain Shuffling (Selection of 95 Clones from Among 960 Clones);

By using, as a model antibody, Rituxan (registered trademark) that has been available on the market, an attempt was made to obtain a whole human antibody having antigenic specificity whose level was equivalent to or higher than that of a chimeric antibody. Note that Rituxan (registered trademark) is an antibody medicine that targets CD20 and that is applied to cell lymphoma. Further, note that an epitope site of CD20 antigen has been already disclosed. Therefore, a fluorescence labeled epitope peptide was prepared by (i) synthesizing only an epitope peptide by solid-phase synthesis and (ii) adding FITC to N terminus of the epitope peptide. Then, this fluorescence labeled epitope peptide was used as an antigen. The following describes a specific procedure.

As a 384-well PS plate for screening, a Black plate (BD Falcon #353285) for fluorescence measurement was used. First, this PS plate was irradiated with oxygen plasma at 30 W for one minute, so that a surface of the PS plate became hydrophilic. After 27 μl of 1.33% Tween PBS was added to each well, 9 μl of the human Fab L-PS library was added to each well. Then, 4 μl of Rituxan (registered trademark) chimeric Fab H-PS was added to each well. Rituxan (registered trademark) chimeric Fab H-PS here had been prepared so that a concentration of the Rituxan (registered trademark) chimeric Fab H-PS was 250 μg/ml in 2 M urea and 1% Tween PBS. Then, two-hour incubation was carried out. Next, after the PS plate was washed with 0.1% Tween PBS, 80 μl of 2% BSA-0.1% Tween PBS was added to each well. Then, the PS plate was subjected to blocking for one hour. Further, after the PS plate was washed with 0.1% Tween PBS, 1 μg/ml FITC labeled antigen solution was prepared. This FITC labeled antigen solution contained 0.1% Tween 20 and 5% human serum. Then, 40 μl of thus prepared FITC labeled antigen solution was added to each well. Then, while light was shielded, one-hour incubation was carried out. Subsequently, after the PS plate was washed with 0.1% Tween PBS, fluorescence intensity was measured by using a fluorescence plate reader (TECAN infinite M200) (excitation wavelength: 486 nm, fluorescence wavelength: 520 nm).

Figure 11:
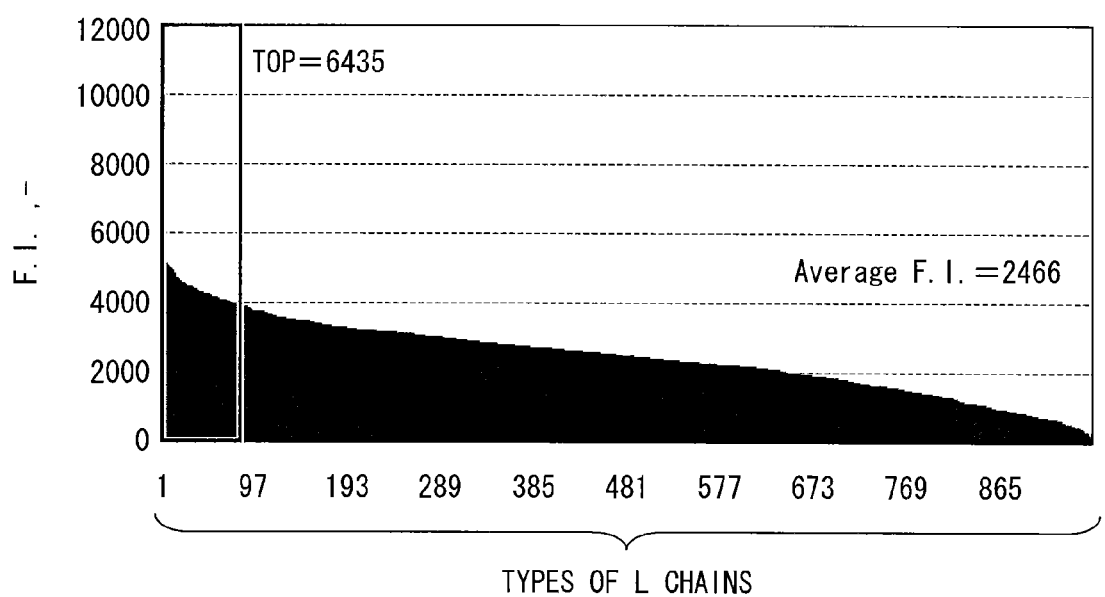
FIG. 11 is a diagram showing a result of examination on combinations of an H chain derived from a chimeric antibody and an L chain selected from a human L chain library (960 types), in regard to affinity for an antigen.

FIG. 11 shows a result of combining a chimeric H chain and a human L chain library (960 types). In FIG. 11, a vertical axis shows fluorescent intensity, while a horizontal axis shows types of human L chains. In regard to combinations of the chimeric H chain and the human L chain library, the highest fluorescence intensity was 6435 while an average fluorescence intensity was 2466. From the human L chains whose fluorescence intensity was 4000 or higher among the 960 clones in combination with the chimeric H chain, top 95 clones in the order of fluorescence intensity detected were selected.

(6) Evaluation of Rituxan (Registered Trademark) Chimeric Fab H-PS/Top 95 Clones of Human Fab L-PS Library by Using In Vitro Domain Shuffling;

In regard to the 95 clones of L chains selected above, evaluation was carried out on relative activity of a single L chain clone and relative activity of a combination of an L chain clone with H chain of the chimeric antibody.

As a 96-well PS plate for screening, a Black plate (Greiner #655076) for fluorescence measurement was used. First, this PS plate was irradiated with oxygen plasma at 30 W for one minute, so that a surface of the PS plate became hydrophilic. Then, each of the top 95 clones of human Fab L-PS and Rituxan (registered trademark) Fab H-PS chimera were mixed and arranged so that: a final concentration of urea was 2 M; a final concentration of Tween 20 was 1%; and a final concentration of chimeric Fab H-PS was 25 µg/ml. As a control, a human Fab L-PS library solution (i.e., that does not contain chimeric Fab H-PS) was prepared. This human Fab L-PS library solution was arranged to have a Tween 20 final concentration of 0.1% and a urea final concentration of 2 M. Then, 100 µl of thus prepared control or thus prepared mixture of a human Fab L-PS clone and Rituxan (registered trademark) Fab H-PS chimera were provided to each well and two-hour incubation was carried out. Then, after the PS plate was washed with 0.1% Tween PBS, 270 µl of 2% BSA-0.1% Tween PBS was added to each well. Next, the PS plate was subjected to blocking for one hour. Further, after the PS plate was washed with 0.1% Tween PBS, 1 µg/ml FITC labeled antigen solution containing 0.1% Tween 20 and 5% human serum was prepared. After 100 µl of thus prepared FITC labeled antigen solution was added to each well, one-hour incubation was carried out while light was shielded. Subsequently, after the PS plate was washed with 0.1% Tween PBS, fluorescence intensity was measured by using a fluorescence plate reader (TECAN infinite M200) (excitation wavelength: 486 nm, fluorescence wavelength: 520 nm).

Figure 12:
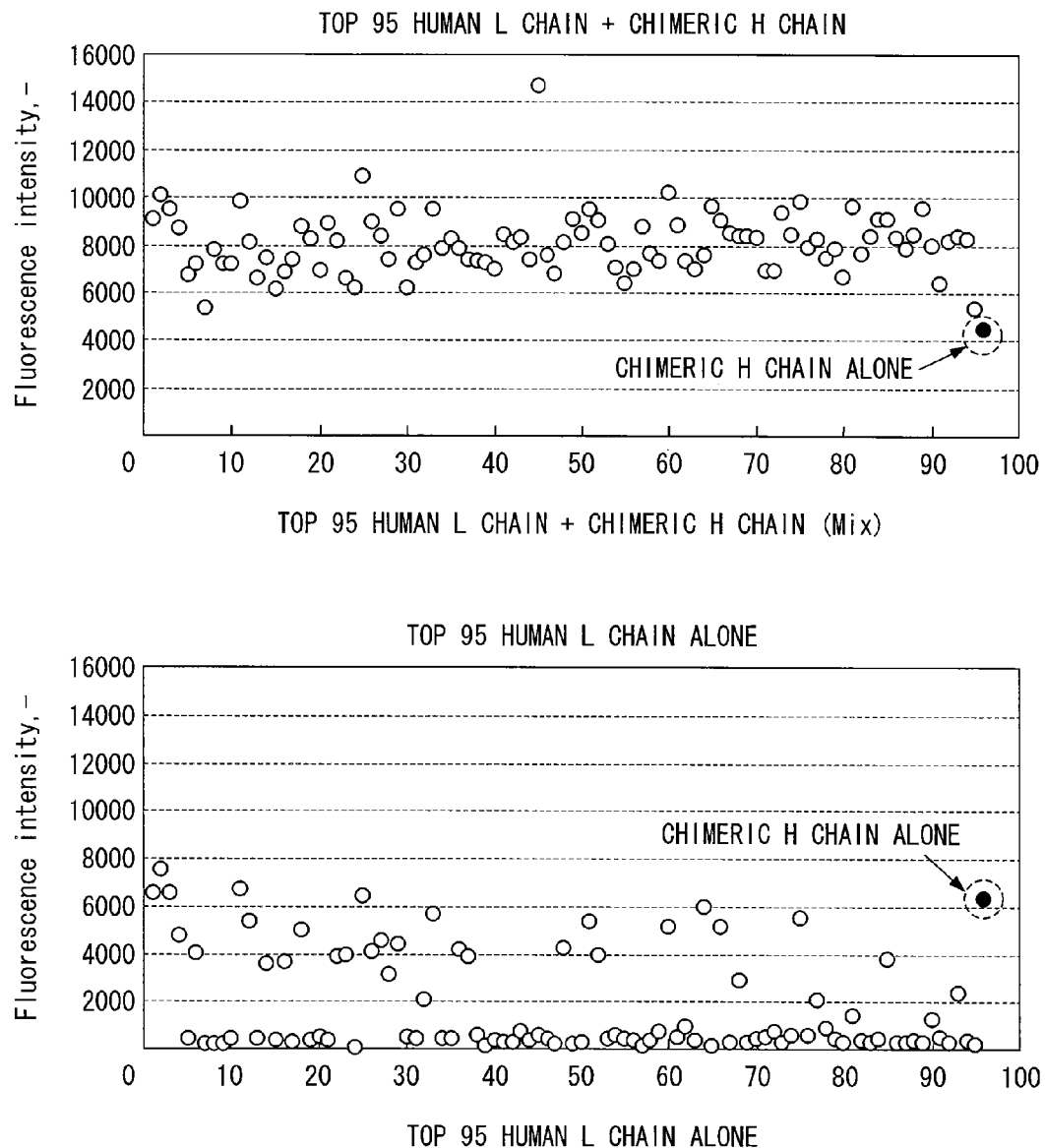
FIG. 12 is a diagram showing a result of examination on top 95 clones from among combinations of an H chain derived from a chimeric antibody and an L chain selected from a human L chain library (960 types), in regard to affinity for an antigen.

FIG. 12 shows a result of the measurement. An upper panel of FIG. 12 shows fluorescence intensity of combinations of each of the top 95 clones of human L chains and H chain of a chimeric antibody. Meanwhile, a lower panel of FIG. 12 shows fluorescence intensity of each single clone of the top 95 clones of human L chains. As shown in the upper panel, among combinations of each of the top 95 clones of human L chains and the chimeric antibody H chain, the fluorescence intensity increased by 6000 or more in 61 clones (63.8%). In 77 clones (81.9%), the fluorescence intensity increased by 4000 or more. In 93 clones (98.9%), the fluorescence intensity increased by 2000 or more. There was a clone whose fluorescence intensity increased by 14131 that was a maximum increase. It became clear that antigen binding ability was significantly improved in many of human L chains screened, in a case where each of the many of human L chains screened was combined with H chain derived from the chimeric antibody.

(7) Evaluation of Human Fab H-PS Library/Rituxan (Registered Trademark) Chimeric Fab L-PS by Using In Vitro Domain Shuffling (Selection of 94 Clones from Among 960 Clones);

Next, by combining L chain of a chimeric antibody and a human H chain library (960 types), a suitable human H chain was screened.

As a 384-well PS plate for screening, a Black plate (BD Falcon #353285) for fluorescence measurement was used. First, this PS plate was irradiated with oxygen plasma at 30 W for one minute, so that a surface of the PS plate became hydrophilic. After 27 µl of 1.33% Tween PBS was added to each well, 9 µl of the human Fab H-PS library was added to each well. Then, 4 µl of Rituxan (registered trademark) chimeric Fab L-PS was added to each well. Rituxan (registered trademark) chimeric Fab L-PS here had been prepared so that a concentration of the Rituxan (registered trademark) chimeric Fab H-PS was 250 µg/ml in 2 M urea and 1 Tween PBS. Then, two-hour incubation was carried out. After the PS plate was washed with 0.1% Tween PBS, 80 µl of 2% BSA-0.1% Tween PBS was added to each well. Then, the PS plate was subjected to blocking for one hour. Further, after the PS plate was washed with 0.1% Tween PBS, 1 µg/ml FITC labeled antigen solution was prepared. This FITC labeled antigen solution contained 0.1% Tween 20 and 5% human serum. Then, 40 µl of thus prepared FITC labeled antigen solution was added to each well. Then, while light was shielded, one-hour incubation was carried out. Subsequently, after the PS plate was washed with 0.1% Tween PBS, fluorescence intensity was measured by using a fluorescence plate reader (TECAN infinite M200) (excitation wavelength: 486 nm, fluorescence wavelength: 520 nm).

Figure 13:
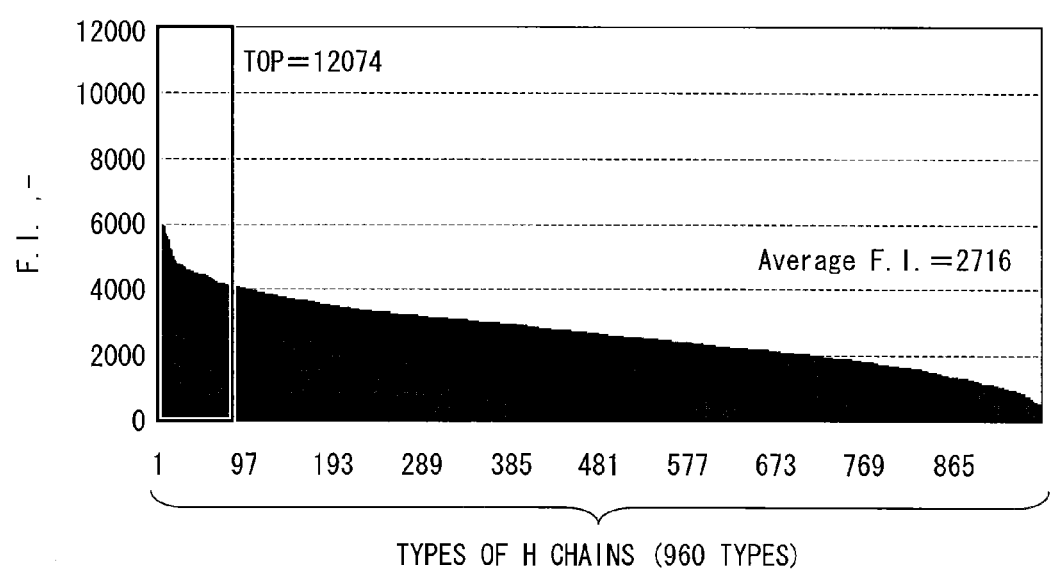
FIG. 13 is a diagram showing a result of examination on combinations of an L chain derived from a chimeric antibody and an H chain selected from a human H chain library (960 types), in regard to affinity for an antigen.

FIG. 13 shows a result of combining L chain derived from a chimeric antibody and a human H chain library (960 types). In FIG. 13, a vertical axis shows fluorescent intensity, while a horizontal axis shows types of human H chains. In regard to combinations of the L chain and the human H chain library, the highest fluorescence intensity was 12074 while an average fluorescence intensity was 2716. From the human H chains whose fluorescence intensity was 4000 or higher among the 960 clones of the human H chains each in combination with the L chain derived from the chimeric antibody, top 94 clones in the order of fluorescence intensity detected were selected.

(8) Evaluation of Top 94 Clones of Human Fab H-PS Library/Rituxan (Registered Trademark) Chimeric Fab L-PS by Using In Vitro Domain Shuffling;

In regard to the 94 clones of H chains selected above, evaluation was carried out on relative activity of a single H chain clone and specific activity of a combination of an H chain clone with L chain of a chimeric antibody.

As a 96-well PS plate for screening, a Black plate (Greiner #655076) for fluorescence measurement was used. First, this PS plate was irradiated with oxygen plasma at 30 W for one minute, so that a surface of the PS plate became hydrophilic. Then, each of the top 94 clones of human Fab H-PS library and Rituxan (registered trademark) Fab L-PS chimera each dissolved in 8 M urea-PBS were mixed and arranged so that: a final concentration of urea was 2 M; a final concentration of Tween 20 was 1%; and a final concentration of chimeric Fab L-PS was 25 µg/ml. As a control, a human Fab H-PS library solution (i.e., that does not contain chimeric Fab L-PS) was prepared. This human Fab H-PS library solution was arranged to have a Tween 20 final concentration of 0.1% and a urea final concentration of 2 M. Then, 100 µl of thus prepared control or thus prepared mixture of a human Fab H-PS clone and Rituxan (registered trademark) Fab L-PS chimera were provided to each well and two-hour incubation was carried out. Then, after the PS plate was washed with 0.1% Tween PBS, 270 µl of 2% BSA-0.1% Tween PBS was added to each well. Next, the PS plate was subjected to blocking for one hour. Further, after the PS plate was washed with 0.1% Tween PBS, 1 µg/ml FITC labeled antigen solution containing 0.1% Tween 20 and 5% human serum was prepared. After 100 µl of thus prepared FITC labeled antigen solution was added to each well, one-hour incubation was carried out while light was shielded. Subsequently, after the PS plate was washed with 0.1% Tween PBS, fluorescence intensity was measured by using a fluorescence plate reader (TECAN infinite M200) (excitation wavelength: 486 nm, fluorescence wavelength: 520 nm).

Figure 14:
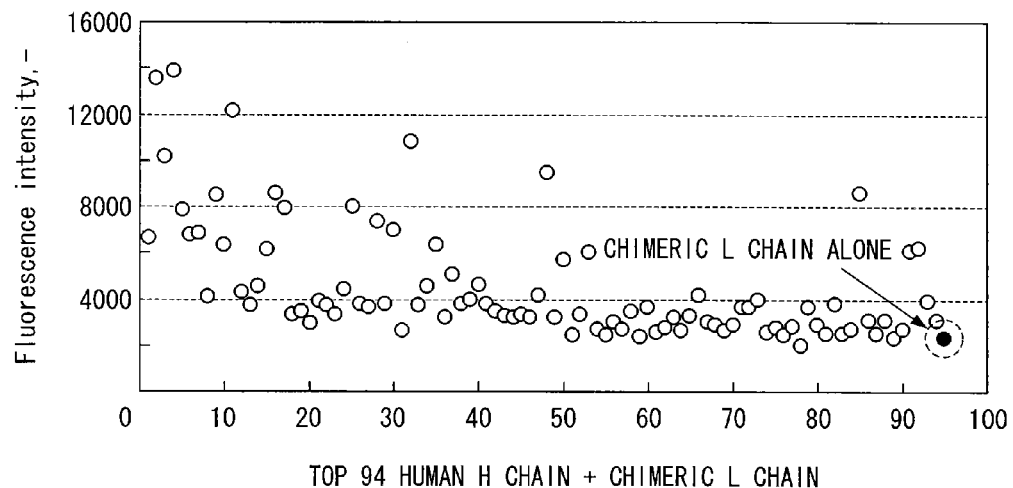
FIG. 14 is a diagram showing a result of examination on top 94 clones from among combinations of an L chain derived from a chimeric antibody and an H chain selected from a human H chain library (960 types), in regard to affinity for an antigen.
Figure 14:
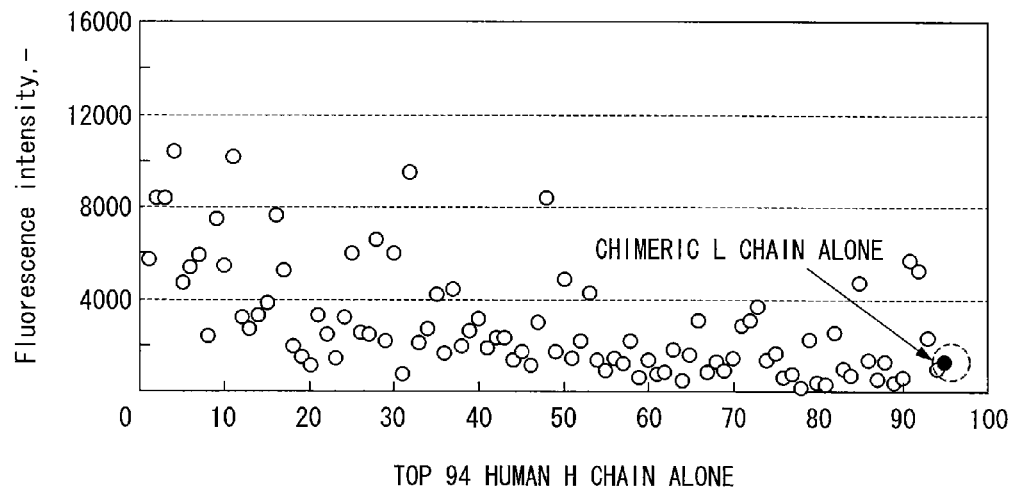

FIG. 14 shows a result of the measurement. An upper panel of FIG. 14 shows fluorescence intensity of combinations of each of the top 94 clones of human H chain and L chain of a chimeric antibody. Meanwhile, a lower panel of FIG. 14 shows fluorescence intensity of each single clone of the top 94 clones of human H chains. As shown in the upper panel, among combinations of each of the top 94 clones of human H chains and the chimeric antibody L chain, the fluorescence intensity increased by 2000 or more in 17 clones (18.1%). In 83 clones (67.0%), the fluorescence intensity increased by 1000 or more. There was a clone whose fluorescence intensity increased by 5272 that was a maximum increase. It became clear that antigen binding ability was significantly improved in many of human H chains screened, in a case where each of the many of human H chains screened was combined with L chain derived from the chimeric antibody.

(9) Evaluation of Human Fab H-PS library/Human Fab L-PS by Using In Vitro Domain Shuffling;

Next, from among the human Fab L-PS and the human Fab H-PS each selected in the above sections (5) to (8), clones having high antigen binding ability were selected. Here, 5 types of human Fab L-PS (Clone No. 1, 2, 3, 11, and 12) and 8 types of human Fab H-PS (Clone No. 1, 2, 3, 4, 11, 32, 48, 85, and 91) were selected. Then, each of 5 the types of human Fab L-PS were combined with every one of the 8 types of human Fab H-PS, and antigen binding ability of thus obtained combinations was evaluated. As a control, Rituxan (registered trademark) chimeric Fab L-PS and chimeric Fab H-PS were used. Clone numbers of the human Fab L-PS indicated here are identical to those in FIGS. 11 and 12. Further, Clone numbers of human Fab H-PS here are identical to those in FIGS. 13 and 14. The following explains a specific procedure.

First, as a 96-well PS plate for screening, a Black plate (Greiner #655076) for fluorescence measurement was used. This PS plate was irradiated with oxygen plasma at 30 W for one minute, so that a surface of the PS plate became hydrophilic. Then, each of (a) each clone of human Fab H-PS, (b) each clone of human Fab L-PS, (c) Rituxan (registered trademark) chimeric Fab L-PS and (c) Rituxan (registered trademark) chimeric Fab H-PS were prepared so that a concentration became 1 mg/l in 8 M urea-PBS-1% Tween 20.

Into each well of a PVC plate, 72 µl of PBS containing 1% Tween 20 and 24 µl of PBS containing 8 M urea and 1% Tween 20 were added. Further, 12 µl of Fab L-PS and 12 µl of Fab H-PS were added to each well (a total amount of solution: 120 µl, a final concentration of Fab L-PS and Fab H-PS: 100 µg/ml, a final concentration of urea: 2 M, and a final concentration of Tween 20:1%). Note that as a control, a sample that contains only one of Fab H-PS and Fab L-PS was also prepared. Then, 100 µl of each of these was added to each well. Subsequently, the Black plate was incubated at 25° C. for 2 hours. Then, after the PS plate was washed with 0.1% Tween PBS, 270 µl of 2% BSA-0.1% Tween PBS was added to each well. Next, the PS plate was subjected to blocking for one hour. Further, after the PS plate was washed with 0.1% Tween PBS, 1 µg/ml FITC labeled antigen solution containing 0.1% Tween 20 and 5% human serum was prepared. After 100 µl of thus prepared FITC labeled antigen solution was added to each well, one-hour incubation was carried out while light was shielded. Subsequently, after the PS plate was washed with 0.1% Tween PBS, fluorescence intensity was measured by using a fluorescence plate reader (TECAN infinite M200) (excitation wavelength: 486 nm, fluorescence wavelength: 520 nm).

Figure 15:
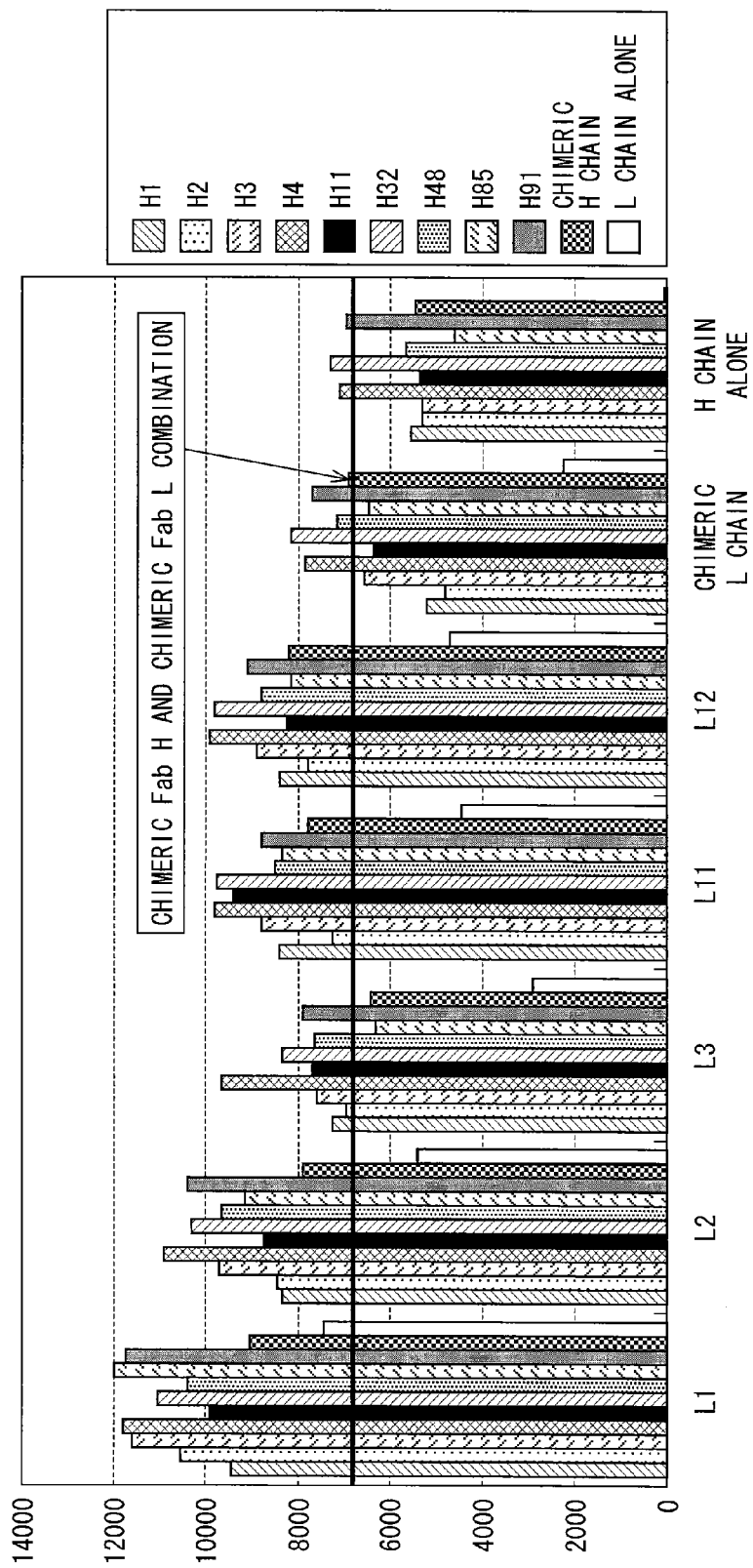
FIG. 15 is a diagram showing a result of examination on combinations (40 types) of a human L chain clone and a human H chain clone, in regard to affinity for an antigen.

On the PS plate, 40 types in total of human Fab were prepared by using the 8 types of human Fab H-PS clones and the 5 types of human Fab L-PS clones. FIG. 15 shows a result of evaluating affinity for FITC labeled antigen. As shown in FIG. 15, there were many combinations of human Fab H-PS and human Fab L-PS each of which combinations shows a higher signal as compared to a combination of chimeric Fab H-PS and chimeric Fab L-PS as a control.

Figure 16:
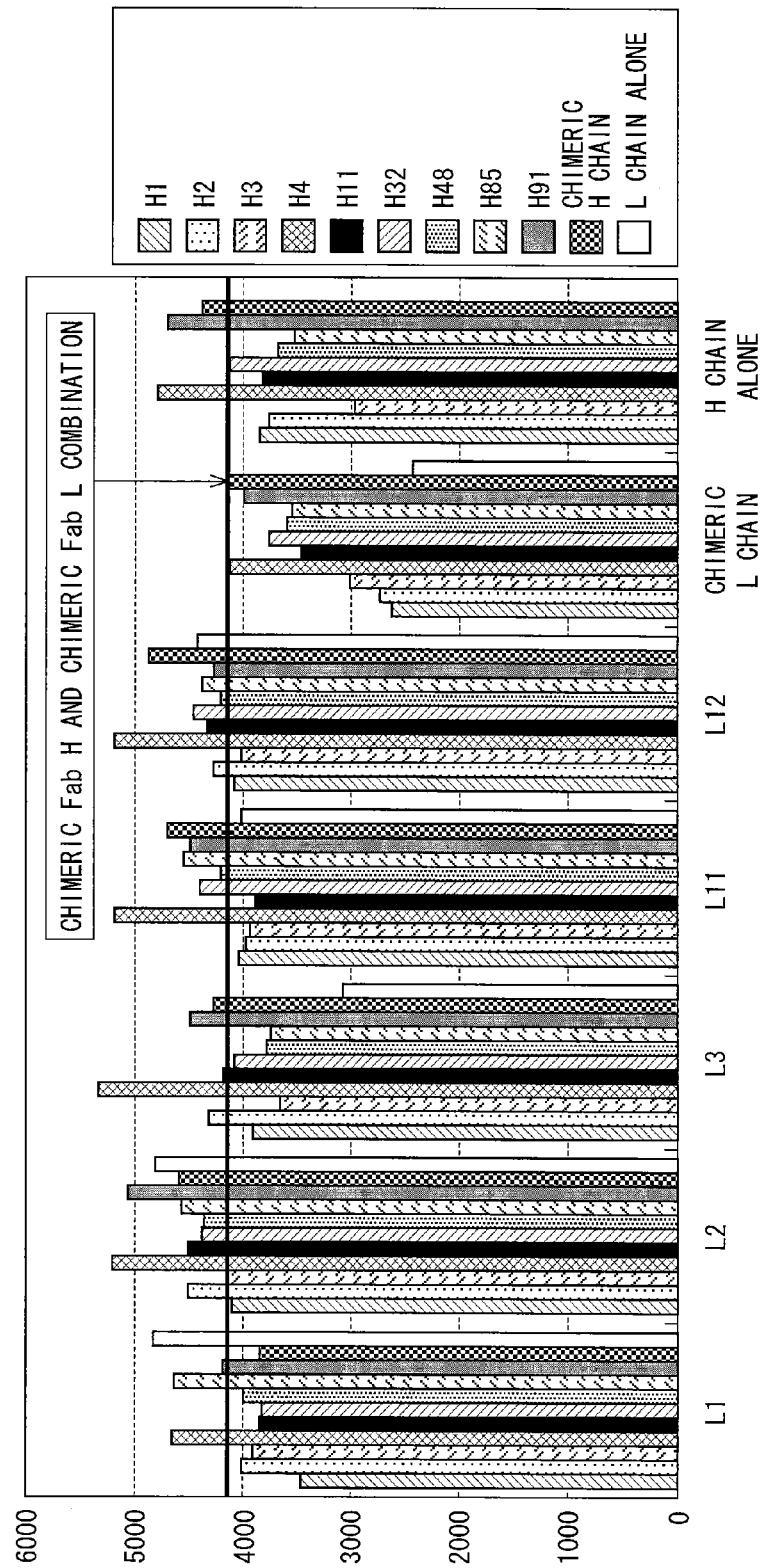
FIG. 16 is a diagram showing a result of examination on combinations (40 types) of a human L chain clone and a human H chain clone, in regard to affinity for an antigen (relative activity; activity per stabilized Fab unit).

FIG. 16 shows a result of calculating specific activity (i.e., signal intensity per unit Fab) obtained by dividing the signal intensity obtained as described above by an amount of Fab H-PS/Fab L-PS immobilized. As shown in FIG. 16, it was possible to obtain many combinations of human Fab H-PS and human Fab L-PS each of which combinations showed specific activity whose level was equivalent to or higher than that of the combination of chimeric Fab H-PS chimeric Fab L-PS. Therefore, it became clear that a whole human antibody could be produced from a chimeric antibody by using the present invention.

(10) Evaluation of Human Fab H-PS/Human Fab L-PS Library by Using In Vitro Domain Shuffling;

In the present experiment, five types (Clone No. 1, 2, 3, 4, and 11) of human Fab H-PS were selected as clones having high antigen binding ability from among clones of human Fab H-PS selected in the sections (5) to (8) above. With respect to each of thus selected 5 types of human Fab H-PS, each of 960 clones of a human Fab L-PS library was combined and affinity for an antigen was evaluated. The following explains a specific procedure.

As a 384-well PS plate for screening, a Black plate (BD Falcon #353285) for fluorescence measurement was used. First, this PS plate was irradiated with oxygen plasma at 30 W for one minute, so that a surface of the PS plate became hydrophilic. After 27 µl of 1.33% Tween PBS was added to each well, 9 µl of the human Fab L-PS library was added to each well. Then, 4 µl of each human Fab H-PS clone was added to each well. The human Fab H-PS clone here had been prepared so that a concentration of the human Fab H-PS clone was 250 µg/ml in 2 M urea and 1% Tween PBS. Then, two-hour incubation was carried out. After the PS plate was washed with 0.1% Tween PBS, 80 µl of 2% BSA-0.1% Tween PBS was added to each well. Then, the PS plate was subjected to blocking for one hour. Further, after the PS plate was washed with 0.1% Tween PBS, 1 µg/ml FITC labeled antigen solution was prepared. This FITC labeled antigen solution contained 0.1% Tween 20 and 5% human serum. Then, 40 µl of thus prepared FITC labeled antigen solution was added to each well. Then, while light was shielded, one-hour incubation was carried out. Ultimately, after the PS plate was washed with 0.1% Tween PBS, fluorescence intensity was measured by using a fluorescence plate reader (TECAN infinite M200) (excitation wavelength: 486 nm, fluorescence wavelength: 520 nm).

(11) Evaluation of Human Fab H-PS Library/Human Fab L-PS by Using In Vitro Domain Shuffling;

Similarly, with respect to top five clones (5 types of human Fab L-PS (Clone No. 1, 2, 3, 11 and 12)) in each of which higher signal intensity was detected in the sections (5) to (8) above, each of 960 clones of a human Fab H-PS library was combined and affinity for an antigen was evaluated. The following explains a specific procedure.

As a 384-well PS plate for screening, a Black plate (BD Falcon #353285) for fluorescence measurement was used. First, this PS plate was irradiated with oxygen plasma at 30 W for one minute, so that a surface of the PS plate became hydrophilic. After 27 µl of 1.33% Tween PBS was added to each well, 9 µl of the human Fab H-PS library was added to each well. Then, 4 µl of each human Fab L-PS clone was added to each well. The human Fab L-PS clone here had been prepared so that a concentration of the human Fab L-PS clone was 250 µg/ml in 2 M urea and 1% Tween PBS. Then, two-hour incubation was carried out. After the PS plate was washed with 0.1% Tween PBS, 80 µl of 2% BSA-0.1% Tween PBS was added to each well. Then, the PS plate was subjected to blocking for one hour. Further, after the PS plate was washed with 0.1% Tween PBS, 1 µg/ml FITC labeled antigen solution was prepared. This FITC labeled antigen solution contained 0.1% Tween 20 and 5% human serum. Then, 40 µl of thus prepared FITC labeled antigen solution was added to each well. Then, while light was shielded, one-hour incubation was carried out. Ultimately, after the PS plate was washed with 0.1% Tween PBS, fluorescence intensity was measured by using a fluorescence plate reader (TECAN infinite M200) (excitation wavelength: 486 nm, fluorescence wavelength: 520 nm).

As described above, 5 types of human Fab H-PS clones and 5 types of human Fab L-PS clones were selected. From thus selected human Fab H-PS clones and human Fab L-PS clones, high detection signals were obtained when each of thus selected human Fab H-PS clones and human Fab L-PS clones was mixed with chimeric Fab H-PS or chimeric Fab L-PS. Each of thus selected five types of human Fab H-PS clones and five types of human Fab L-PS clones was set together thoroughly with every one of 960 clones of the human Fab L-PS library or each of 960 clones of the human Fab H-PS library. Thereby, 9600 types of Fab antibodies each made of human Fab H-PS and human Fab L-PS were prepared on a PS plate. In regard to the above human Fab H-PS and human Fab L-PS, affinity for a fluorescence labeled antigen was evaluated. FIGS. 17 to 22 show results of the evaluation.

Figure 17:
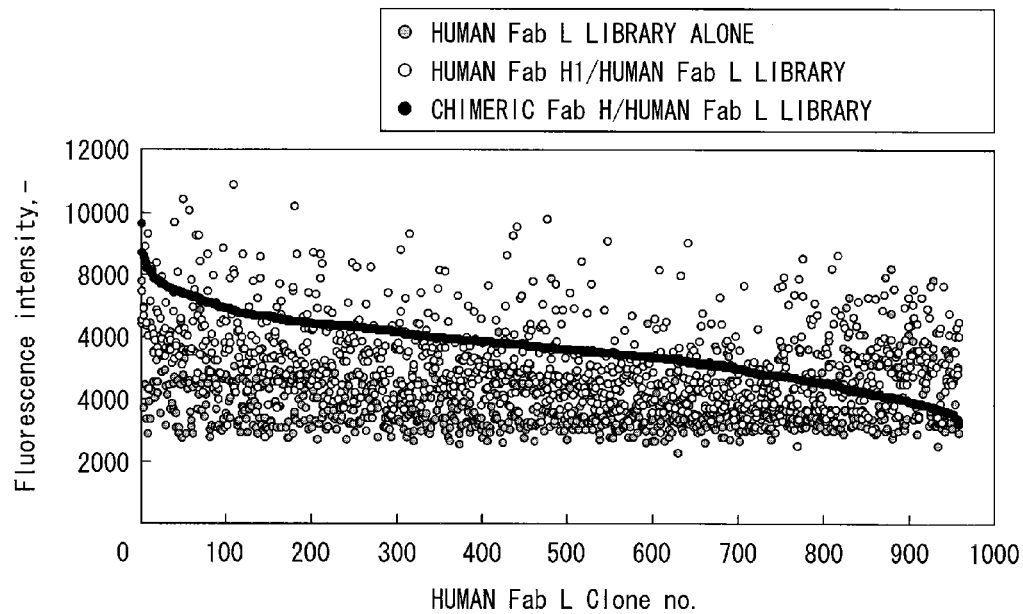
FIG. 17 is a diagram showing (a) in an upper panel, a result of Fab antibodies obtained by combining 960 types in a human Fab L-PS library with Clone No. 1 of human Fab H-PS and (b) in a lower panel, a result of Fab antibodies obtained by combining 960 types in a human Fab L-PS library with Clone No. 2 of human Fab H-PS.
Figure 17:
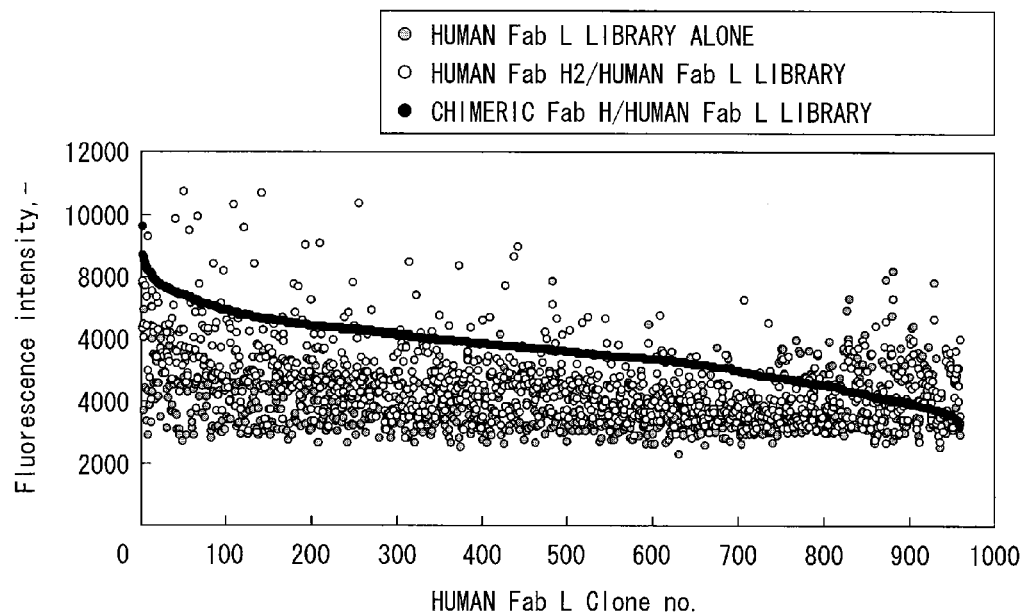
Figure 18:
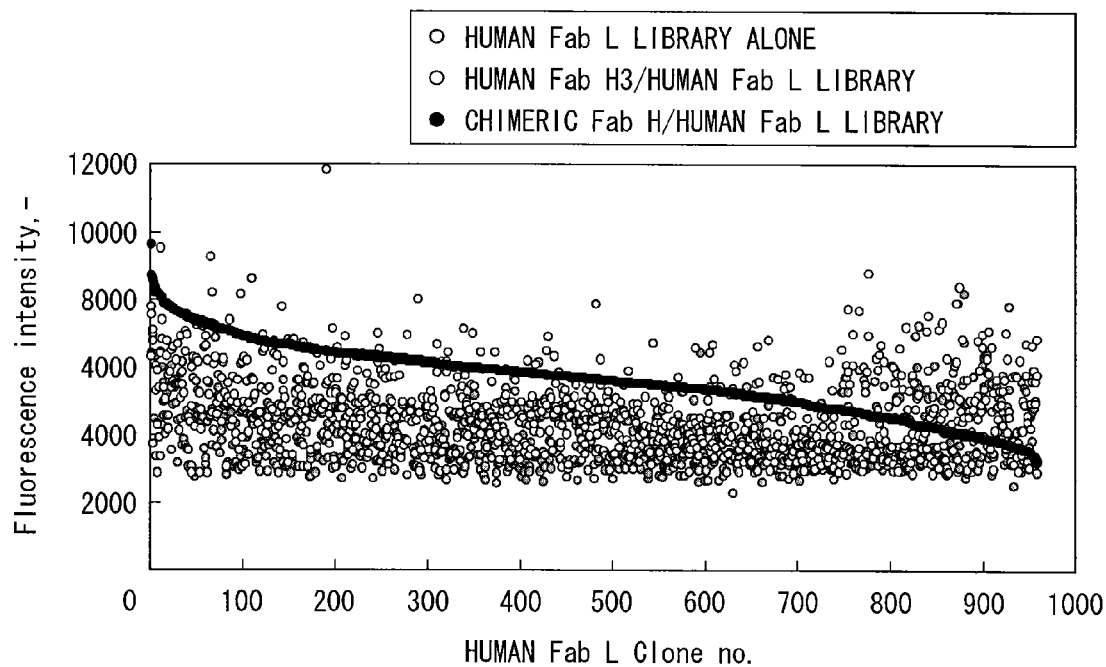
FIG. 18 is a diagram showing (a) in an upper panel, a result of Fab antibodies obtained by combining 960 types in a human Fab L-PS library with Clone No. 3 of human Fab H-PS and (b) in a lower panel, a result of Fab antibodies obtained by combining 960 types in a human Fab L-PS library with Clone No. 4 of human Fab H-PS.
Figure 18:
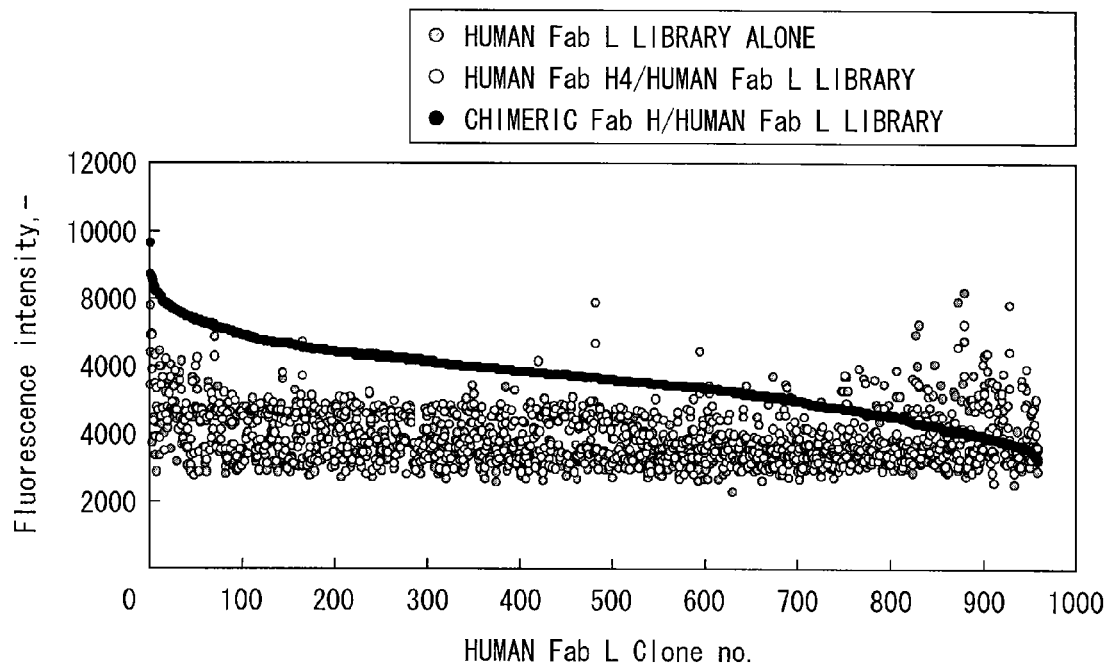
Figure 19:
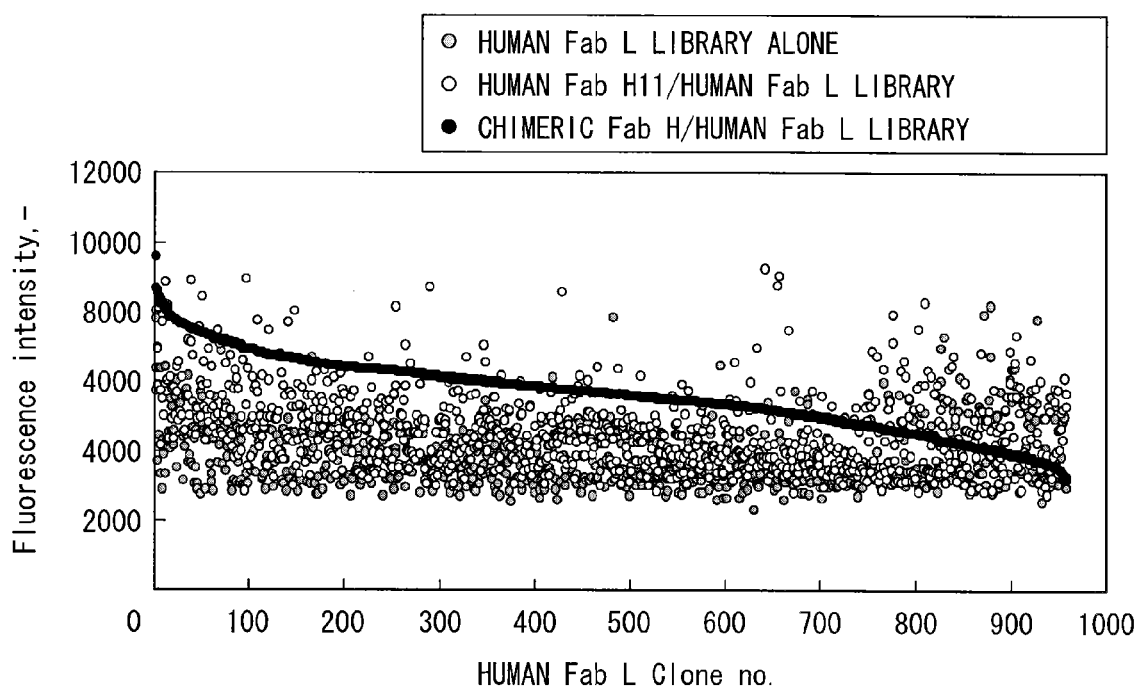
FIG. 19 is a diagram showing a result of Fab antibodies obtained by combining 960 types in a human Fab L-PS library with Clone No. 11 of human Fab H-PS.

More specifically, FIG. 17 shows (a) in an upper panel, a result of Fab antibodies obtained by combining 960 types in a human Fab L-PS library with Clone No. 1 of human Fab H-PS and (b) in a lower panel, a result of Fab antibodies obtained by combining 960 types in a human Fab L-PS library with Clone No. 2 of human Fab H-PS. Similarly, FIG. 18 shows (a) in an upper panel, a result of Fab antibodies obtained by combining 960 types in a human Fab L-PS library with Clone No. 3 of human Fab H-PS and (b) in a lower panel, a result of Fab antibodies obtained by combining 960 types in a human Fab L-PS library with Clone No. 4 of human Fab H-PS. FIG. 19 shows a result of Fab antibodies obtained by combining 960 types in a human Fab L-PS library with Clone No. 11 of human Fab H-PS.

Figure 20:
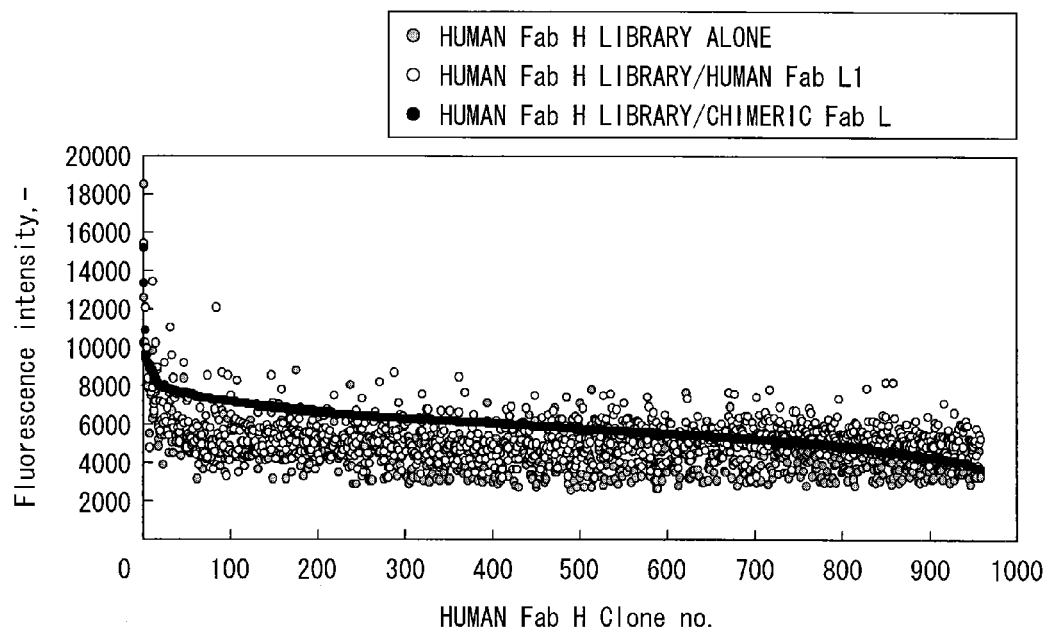
FIG. 20 is a diagram showing (a) in an upper panel, a result of Fab antibodies obtained by combining 960 types in a human Fab H-PS library with Clone No. 1 of human Fab L-PS and (b) in a lower panel, a result of Fab antibodies obtained by combining 960 types in a human Fab H-PS library with Clone No. 2 of human Fab L-PS.
Figure 20:
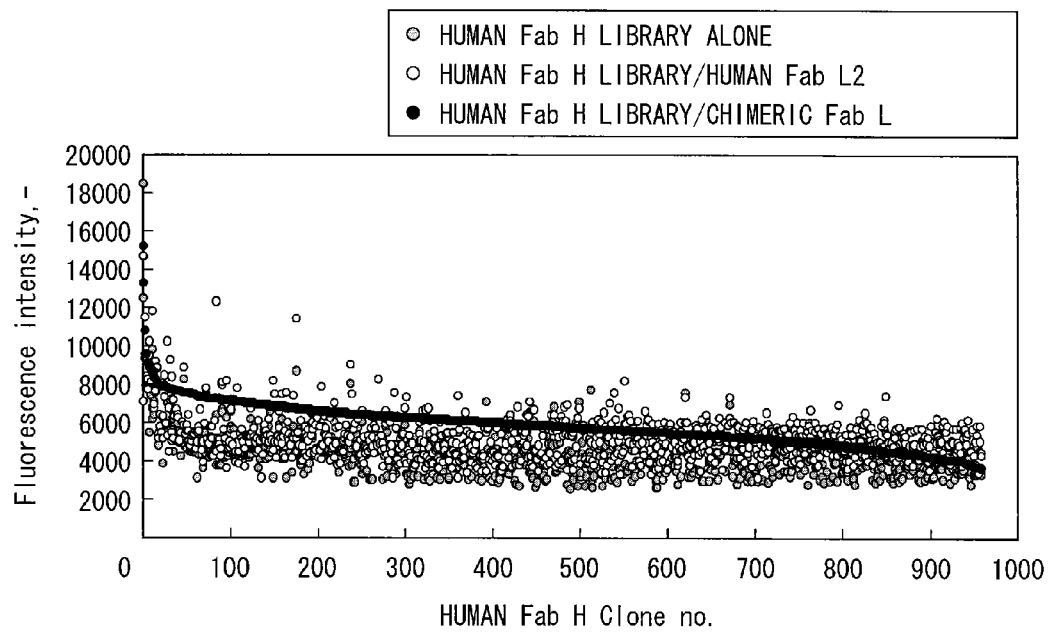
Figure 21:
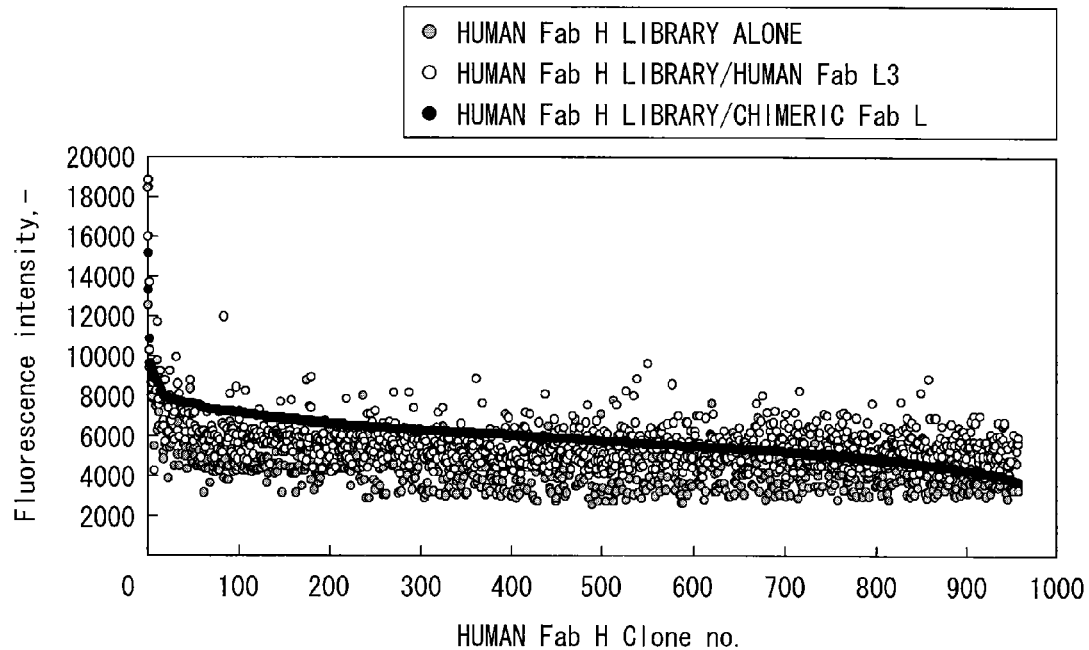
FIG. 21 is a diagram showing (a) in an upper panel, a result of Fab antibodies obtained by combining 960 types in a human Fab H-PS library with Clone No. 3 of human Fab L-PS and (b) in a lower panel, a result of Fab antibodies obtained by combining 960 types in a human Fab H-PS library with Clone No. 11 of human Fab L-PS.
Figure 21:
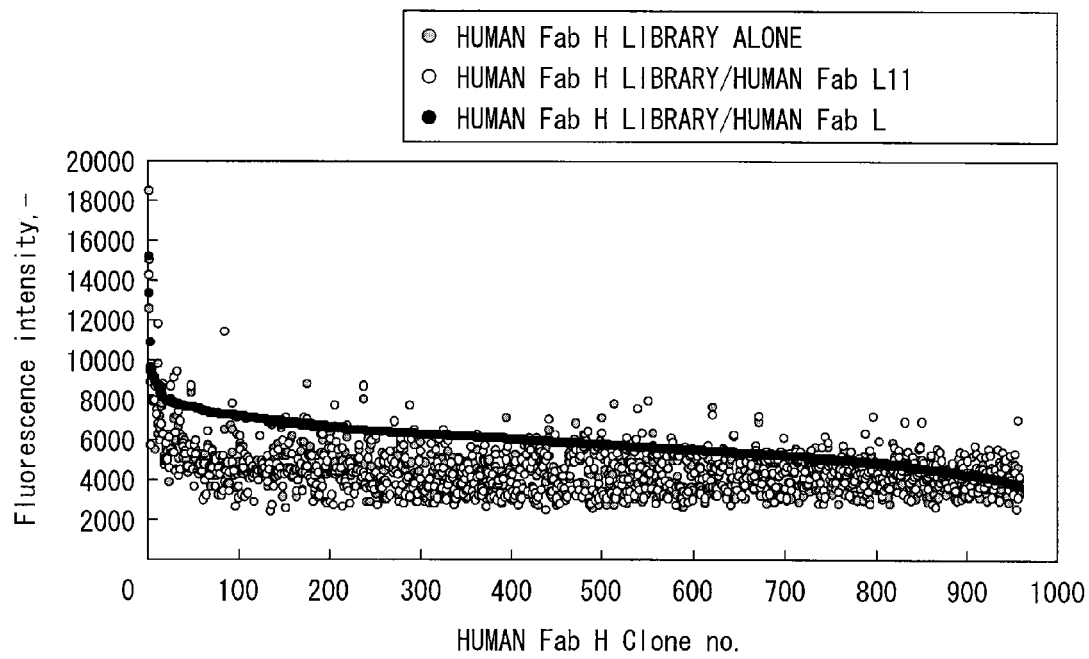
Figure 22:
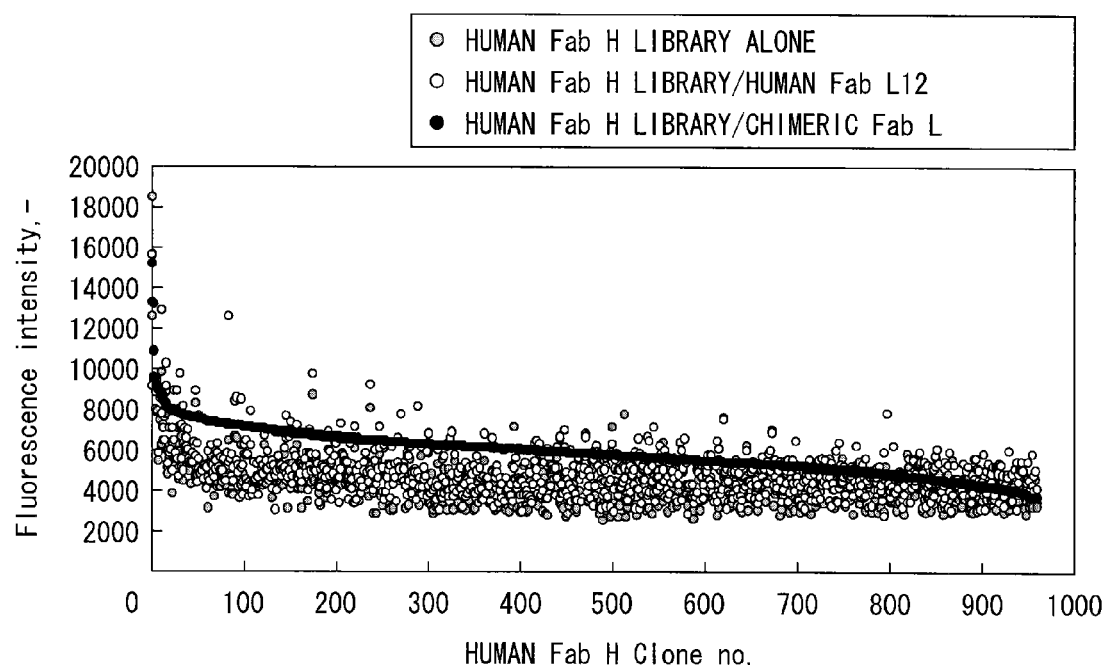
FIG. 22 is a diagram showing a result of Fab antibodies obtained by combining 960 types in a human Fab H-PS library with Clone No. 12 of human Fab L-PS.

Moreover, FIG. 20 shows (a) in an upper panel, a result of Fab antibodies obtained by combining 960 types in a human Fab H-PS library with Clone No. 1 of human Fab L-PS and (b) in a lower panel, a result of Fab antibodies obtained by combining 960 types in a human Fab H-PS library with Clone No. 2 of human Fab L-PS. FIG. 21 shows (a) in an upper panel, a result of Fab antibodies obtained by combining 960 types in a human Fab H-PS library with Clone No. 3 of human Fab L-PS and (b) in a lower panel, a result of Fab antibodies obtained by combining 960 types in a human Fab H-PS library with Clone No. 11 of human Fab L-PS. FIG. 22 shows a result of Fab antibodies obtained by combining 960 types in a human Fab H-PS library with Clone No. 12 of human Fab L-PS.

As shown in the above drawings, many combinations of human Fab H-PS and human Fab L-PS were detected as combinations each having a signal whose level was equivalent to or higher than that of a Fab antibody made of a combination of chimeric Fab H-PS and human Fab L-PS or a combination of human Fab H-PS and chimeric Fab L-PS. In particular, it is highly likely that very high affinity for an antigen is held by the combinations of human Fab H-PS and human Fab L-PS from each of which combinations a signal intensity of 10000 or higher was obtained. Therefore, detailed affinity evaluation will make it possible to obtain a whole human antibody clone that has higher affinity and less adverse effect as compared to a chimeric antibody made of chimeric Fab H-PS and chimeric Fab L-PS.

INDUSTRIAL APPLICABILITY

The present invention is applicable as a basic technology for antibody screening. By obtaining a whole antibody by recloning of a heavy-chain low-molecular-weight antibody and a light-chain low-molecular-weight antibody each screened as described above, thus obtained whole antibody may be used, for example, for an antibody drug or a diagnostic product.

The invention claimed is:

1. An antibody-immobilized carrier comprising at least two antibody immobilized regions, wherein each of said antibody immobilized regions comprises
   a carrier binding peptide bound to the material of a carrier surface and to the C-terminus side of the heavy-chain variable region within a heavy-chain low-molecular-weight antibody, and
   a separate carrier binding peptide bound to the material of a carrier surface and the C-terminus side of the light-chain variable region within a light-chain low-molecular-weight antibody,
   wherein said heavy-chain low-molecular-weight antibody and said light-chain low-molecular-weight antibody within said antibody immobilized region recognize different antigens,
   wherein each of said antibody immobilized regions are configured such that an antigen may simultaneously bind said variable region of said heavy-chain low molecular-weight antibody and said variable region of said light-chain low molecular-weight antibody within said antibody immobilized region,
   wherein the material of the carrier surface is selected from the group consisting of a polystyrene plastic resin, a polycarbonate plastic resin, a polymethyl methacrylate plastic resin, a plastic resin obtained through hydrophilizing a polystyrene plastic resin, a plastic resin obtained through hydrophilizing a polycarbonate plastic resin, and a plastic resin obtained through hydrophilizing a polymethyl methacrylate plastic resin and wherein the carrier binding peptide is selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19.

2. The antibody-immobilized carrier as set forth in claim 1, wherein:
   the carrier binding peptide is a peptide that binds to hydrophilic polystyrene, hydrophilic polycarbonate, or hydrophilic polymethyl methacrylate.

3. The antibody-immobilized carrier as set forth in claim 1, wherein:
   the heavy-chain low-molecular-weight antibody is a heavy-chain low-molecular-weight antibody consisting of the heavy-chain variable region or a heavy-chain low-molecular-weight antibody consisting of a heavy-chain variable region and a first heavy-chain constant region.

4. The antibody-immobilized carrier as set forth in claim 1, comprising at least $10^2$ antibody immobilized regions.

5. The antibody-immobilized carrier as set forth in claim 1, wherein the antibody immobilized region includes a region in which the heavy-chain low-molecular-weight antibody and the light-chain low-molecular-weight antibody form a pair.

6. The antibody-immobilized carrier as set forth in claim 1, wherein each of said antibody immobilized regions are not identical.

7. The antibody-immobilized carrier as set forth in claim 1, wherein said material is a polystyrene plastic resin or a plastic resin obtained through hydrophilizing a polystyrene plastic resin.

8. The antibody-immobilized carrier as set forth in claim 1, wherein said carrier binding peptide is a polystyrene binding peptide.

9. The antibody-immobilized carrier as set forth in claim 8, wherein said polystyrene binding peptide comprises SEQ ID NO. 11.

10. The antibody-immobilized carrier as set forth in claim 1, wherein the material of the carrier surface is a polymethyl methacrylate plastic resin or a plastic resin obtained through hydrophilizing a polymethyl methacrylate plastic resin.

11. The antibody-immobilized carrier as set forth in claim 10, wherein said carrier binding peptide is a polymethyl methacrylate binding peptide.

12. The antibody-immobilized carrier as set forth in claim 11, wherein the polymethyl methacrylate binding peptide comprises an amino acid sequence selected from the group consisting of SEQ ID NO: 15, SEQ ID NO: 18, and SEQ ID NO: 19.

13. The antibody-immobilized carrier as set forth in claim 1, wherein the material of the carrier surface is a polycarbonate plastic resin or a plastic resin obtained through hydrophilizing a polycarbonate plastic resin.

14. The antibody-immobilized carrier as set forth in claim 13, wherein said carrier binding peptide is a polycarbonate binding peptide.

15. The antibody-immobilized carrier as set forth in claim 14, wherein the polycarbonate binding peptide comprises an amino acid sequence selected from the group consisting of SEQ ID NO: 12, SEQ ID NO: 13, SEQ ID NO: 14, SEQ ID NO: 15, SEQ ID NO: 16, and SEQ ID NO: 17.

* * * * *